US010362955B2

(12) United States Patent
Arunachalam et al.

(10) Patent No.: US 10,362,955 B2
(45) Date of Patent: Jul. 30, 2019

(54) GRAPHICALLY MAPPING ROTORS IN A HEART

(71) Applicant: Regents of the University of Minnesota, Minneapolis, MN (US)

(72) Inventors: Shivaram Poigai Arunachalam, Minneapolis, MN (US); Alena Talkachova, Minneapolis, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 32 days.

(21) Appl. No.: 15/427,349

(22) Filed: Feb. 8, 2017

(65) Prior Publication Data

US 2017/0224238 A1 Aug. 10, 2017

Related U.S. Application Data

(60) Provisional application No. 62/293,563, filed on Feb. 10, 2016, provisional application No. 62/296,418, filed on Feb. 17, 2016.

(51) Int. Cl.
*A61B 5/0452* (2006.01)
*A61B 5/046* (2006.01)
(Continued)

(52) U.S. Cl.
CPC .............. *A61B 5/046* (2013.01); *A61B 5/044* (2013.01); *A61B 5/04017* (2013.01); *A61B 5/7253* (2013.01)

(58) Field of Classification Search
None
See application file for complete search history.

(56) References Cited

U.S. PATENT DOCUMENTS 9,433,365 B1* 9/2016 Lin ................... A61B 5/04012
2009/0088633 A1* 4/2009 Meyer ..................... A61B 6/12
600/424

(Continued)

OTHER PUBLICATIONS

Oral et al., "Circumferential Pulmonary-Vein Ablation for Chronic Atrial Fibrillation", N Engl J Med 2006;354;9 pp. 934-941, [PubMed: 16510747].

(Continued)

*Primary Examiner* — Kennedy Schaetzle
(74) *Attorney, Agent, or Firm* — Brian D. Kaul; Westman, Champlin & Koehler, P.A.

(57) ABSTRACT

Disclosed herein are techniques for graphically indicating aspects of rotors (such as pivot points of rotors) associated with atrial or ventricular fibrillation. Embodiments can include receiving, using a processor, an electrogram for each of a plurality of spatial locations in a heart, each electrogram comprising time series data including a plurality of electrical potential readings over time. Embodiments can also include generating, from the time series data, one or more of multi-scale frequency (MSF), kurtosis, empirical mode decomposition (EMD), and multi-scale entropy (MSE) datasets, each dataset including a plurality of respective values or levels corresponding to the plurality of spatial locations in the heart. Also, examples can include generating, from the one or more datasets, a map including a plurality of graphical indications of the values or levels at the plurality of spatial locations in the heart, wherein the map can include an image of the heart and graphical indications of locations of aspects of rotors in the heart (such as pivot point of rotors).

19 Claims, 23 Drawing Sheets

(51) Int. Cl.
A61B 5/04 (2006.01)
A61B 5/00 (2006.01)
A61B 5/044 (2006.01)

(56) References Cited

U.S. PATENT DOCUMENTS

| | | | | |
|---|---|---|---|---|
| 2012/0232417 | A1* | 9/2012 | Zhang | A61N 1/3702 600/518 |
| 2013/0197380 | A1* | 8/2013 | Oral | A61B 5/0452 600/518 |
| 2015/0230721 | A1* | 8/2015 | Lo | A61B 5/04011 600/512 |
| 2015/0366476 | A1* | 12/2015 | Laughner | A61B 5/743 600/374 |
| 2017/0303807 | A1* | 10/2017 | Laughner | A61B 5/6858 |

OTHER PUBLICATIONS

Sanders et al., "Spectral Analysis Identifies Sites of High-Frequency Activity Maintaining Atrial Fibrillation in Humans", Circulation. Aug. 9, 2005;112(6):789-797.
Sharma et al., "Kurtosis based Multichannel ECG Signal Denoising and Diagnostic Distortion Measures", TENCON 2009 IEEE Region 10 Conference Jan. 23, 2009 (pp. 1-5).
Tzou et al., "Termination of Persistent Atrial Fibrillation During Left Atrial Mapping", J Cardiovasc Electrophysiol, vol. 22, pp. 1171-1173, Oct. 2011.
Lim et al., "Medium-Term Efficacy of Segmental Ostial Pulmonary Vein Isolation for the Treatment of Permanent and Persistent Atrial Fibrillation", PACE, Apr. 1, 2006;29(4):374-379.
Kanagaratnam et al., "Empirical Pulmonary Vein Isolation in Patients with Chronic Atrial Fibrillation Using a Three-Dimensional Nonfluoroscopic Mapping System: Long-Term Follow-Up", PACE, Dec. 1, 2001;24(12):177-1779.
Akoum et al., "Atrial Fibrosis Helps Select the Appropriate Patient and Strategy in Catheter Ablation of Atrial Fibrillation: A DE-MRI Guided Approach", Journal of cardiovascular electrophysiology, 2011, vol. 22, No. 1, pp. 16-22.
Allessie et al., "Crosstalk opposing view: Rotors have not been demonstrated to be the drivers of atrial fibrillation", The Journal of Physiology, 2014, vol. 592, No. 15, pp. 3167-3170.
Andrade et al., "The Clinical Profile and Pathophysiology of Atrial Fibrillation Relationships Among Clinical Features, Epidemiology, and Mechanisms", Circulation research, 2014, vol. 114, No. 9, pp. 1453-1468.
Arunachalam et al., "Feasibility of visualizing higher regions of Shannon Entropy in Atrial Fibrillation patients", In Engineering in Medicine and Biology Society (EMBS), 2015 37th Annual International Conference of the IEEE, pp. 4499-4502, 2015.
Arunachalam et al., "Kurtosis as a Statistical Approach to Identify the Pivot Point of the Rotor", In Engineering in Medicine and Biology Society (EMBC), IEEE 38th Annual International Conference of the 2016, pp. 497-500, 2016.
Arunachalam et al., "Novel Multiscale Frequency Approach to Identify the Pivot Point of the Rotor", Journal of Medical Devices, vol. 10, No. 2, 2 pages, 2016.
Arunachalam et al., "Rotor Pivot Point Identification with Intrinsic Mode Function Complexity Index using Empirical Mode Decomposition", In Student Conference (ISC), IEEE EMBS International May 2016 (pp. 1-4), 2016.
Ashihara et al., "The Role of Fibroblasts in Complex Fractionated Electrograms During Persistent/Permanent Atrial Fibrillation Implications for Electrogram-Based Catheter Ablation", Circulation research, vol. 110, No. 2, pp. 275-284, 2012.
Atienza et al., "Real-time Dominant Frequency Mapping and Ablation of Dominant-Frequency Sites in Atrial Fibrillation with Left-to-Right Frequency Gradients Predicts Long-Term Maintenance of Sinus Rhythm", Heart Rhythm, vol. 6, No. 1, pp. 33-40, 2009.

Bandt et al., "Permutation entropy: a natural complexity measure for time series", Physical Review Letters, 5 pages, 2002.
Baumert et al., "Quantitative-Electrogram-Based Methods for Guiding Catheter Ablation in Atrial Fibrillation", Proceedings of the IEEE, vol. 104, No. 2., pp. 416-431, 2016.
Benharash et al., "Quantitative Analysis of Localized Sources Identified by Focal Impulse and Rotor Modulation Mapping in Atrial Fibrillation", Circ Arrhythm Electrophysiol, vol. 8, No. 3, pp. 554-561, 2015.
Brown, "Managing a Multicenter Clinical Research Study: The CABANA Trial: Catheter Ablation Versus Drug Therapy for the Treatment of Atrial Fibrillation", Theses and Dissertations, 75 pages, 2009.
Buch et al., "Long-term clinical outcomes of focal impulse and rotor modulation for treatment of atrial fibrillation: A multicenter experience", Heart Rhythm,. vol. 13, No. 3, pp. 636-641, 2016.
Calkins et al., "2012 HRS/EHRA/ECAS Expert Consensus Statement on Catheter and Surgical Ablation of Atrial Fibrillation: Recommendations for Patient Selection, Procedural Techniques, Patient Management and Follow-up, Definitions, Endpoints, and Research Trial Design", Heart Rhythm, vol. 9, pp. 632-696.e621, 2012.
Chao et al., "Clinical Outcome of Catheter Ablation in Patients With Nonparoxysmal Atrial Fibrillation: Results of 3-year Follow-Up", Circ Arrhythm Electrophysiol, vol. 5, pp. 514-520, 2012.
Chen et al., "Epidemiology of atrial fibrillation: a current perspective", Heart Rhythm, vol. 4, No. 3, pp. S1-S6, 2007.
Chou et al., "Epicardial Ablation of Rotors Suppresses Inducibility of Acetylcholine-Induced Atrial Fibrillation in Left Pulmonary Vein-Left Atrium Preparations in a Beagle Heart Failure Model", Journal of the American College of Cardiology, vol. 58, No. 2, pp. 158-166, 2011.
Chugh et al., "Worldwide Epidemiology of Atrial Fibrillation: a Global Burden of Disease 2010 Study". Circulation vol. 129, No. 8, pp. 837-847, 2014.
Costa et al., "Multiscale Entropy Analysis of Complex Physiologic Time Series", Physical Review Letters, vol. 89, No. 6, pp. 068102-1-068102-4, 2002.
Davidenko et al., "Stationary and drifting spiral waves of excitation in isolated cardiac muscle", Nature, vol. 355, pp. 349-351, 1992.
Dixit et al., "Catheter Ablation for Persistent Atrial Fibrillation Antral Pulmonary Vein Isolation and Elimination of Nonpulmonary Vein Triggers Are Sufficient", Circulation Arrhythmia Electrophysiology, vol. 5, No. 6, pp. 1216-1223, 2012.
Earley et al., "Validation of the Noncontact Mapping System in the Left Atrium During Permanent Atrial Fibrillation and Sinus Rhythm", Journal of the American College of Cardiology, vol. 48, No. 3, pp. 485-491, 2006.
Elayi et al., "Atrial fibrillation termination as a procedural endpoint during ablation in long-standing persistent atrial fibrillation", Heart Rhythm, vol. 7, pp. 1216-1223, 2010.
Ganesan et al., "Bipolar Electrogram Shannon Entropy at Sites of Rotational Activation Implications for Ablation of Atrial Fibrillation", Circulation: Arrhythmia and Electrophysiology, vol. 6, No. 1, pp. 48-57, 2013.
Ganesan et al., "Long-term Outcomes of Catheter Ablation of Atrial Fibrillation: A Systematic Review and Meta-analysis", Journal of the American Heart Association, vol. 2, No. 2, e004549-1-e004549-14, 2013.
Guillem et al., "Presence and Stability of Rotors in Atrial Fibrillation: Evidence and Therapeutic Implications", Cardiovascular research, 46 pages, 2016.
Habel et al., "The temporal variability of dominant frequency and complex fractionated atrial electrograms constrains be validity of sequential mapping in human atrial fibrillation", Heart Rhythm, vol. 7, No. 5, pp. 586-593, 2010.
Haissaguerre et al., "Spontaneous Initiation of Atrial Fibrillation by Ectopic Beats Originating in the Pulmonary Veins", The New England Journal of Medicine, vol. 339, No. 10, pp. 659-666, 1998.
Haissaguerre et al., "Catheter Ablation of Long-Lasting Persistent Atrial Fibrillation: Critical Structures for Termination", Journal of Cardiovascular Electrophysiology, vol. 16, No. 11, pp. 1125-1137, 2005.

(56) References Cited

OTHER PUBLICATIONS

Haissaguerre et al., "Mapping-Guided Ablation of Pulmonary Veins to Cure Atrial Fibrillation", The American Journal of Cardiology, vol. 86, No. 9A, pp. 9K-19K, 2000.
Herweg et al., "Termination of Persistent Atrial Fibrillation Resistant to Cardioversion by a Single Radiofrequency Application", Pacing Clin Electrophysiol, vol. 26, pp. 1420-1423, 2003.
Huang et al., "The empirical mode decomposition and the Hilbert spectrum for nonlinear and non-stationary time series analysis", Proceedings of the Royal Society, London, Ser. A, vol. 454, pp. 903-995, 1998.
Jalife et al., "Mother rotors and fibrillatory conduction: a mechanism of atrial fibrillation", Cardiovascular research, vol. 54, No. 2, pp. 204-216, 2002.
January et al., "2014 AHA/ACC/HRS guideline for the management of patients with atrial fibrillation: A report of the American College of Cardiology/American Heart Association Task Force on Practice Guidelines and the Heart Rhythm Society," Journal of American College Cardiology., vol. 64, pp. e199-e211, 2014.
Kim et al., "Estimation of Total Incremental Health Care Costs in Patients With Atrial Fibrillation in the United States", Circulation: Cardiovascular Quality and Outcomes, vol. 4, No. 3, pp. 313-320, 2011.
Knutsson et al., "Local Multiscale Frequency and Bandwidth Estimation", in Image Processing, 1994, Proceedings. ICIP-94., IEEE International Conference, vol. 1, pp. 36-40. IEEE, 1994.
Krummen et al., "The role of rotors in atrial fibrillation", Journal of thoracic disease, vol. 7, No. 2, pp. 142-151, 2015.
Lin et al., "Prevalence, Characteristics, Mapping, and Catheter Ablation of Potential Rotors in Non-Paroxysmal Atrial Fibrillation", Circulation: Arrhythmia and Electrophysiology, 2013, vol. 6, No. 5, 34 pages.
Lloyd-Jones et al., "Lifetime Risk for Development of Atrial Fibrillation: The Framingham Heart Study," Circulation, vol. 110, pp. 1042-1046, 2004.
Mandapati et al., "Stable Microreentrant Sources as a Mechanism of Atrial Fibrillation in the Isolated Sheep Heart", Circulation, vol. 101, No. 2, pp. 194-199, 2000.
Matiukas et al., "E.G. Optical Mapping of Electrical Heterogeneities in the Heart During Global Ischemia",31st Annual International Conference of the IEEE Eng Med Biol Soc 1, 6321-6324 (2009).
Medi et al., "Pulmonary Vein Antral Isolation for Paroxysmal Atrial Fibrillation: Results from Long-Term Follow-Up", Journal of Cardiovascular Electrophysiology, vol. 22, No. 2, pp. 137-141, 2011.
Mironov et al., "Role of Conduction Velocity Restitution and Short-Term Memory in the Development of Action Potential Duration Alternans in Isolated Rabbit Hearts", Circulation, vol. 118, No. 1, pp. 17-25, 2008.
Moe et al., "A computer model of atrial fibrillation", American Heart Journal, vol. 67, No. 2, pp. 200-220, 1964.
Nademanee et al., "A New Approach for Catheter Ablation of Atrial Fibrillation: Mapping of the Electrophysiologic Substrate", Journal of the American College of Cardiology, vol. 43, No. 11, 2004, pp. 2044-2053.
Narayan et al., "Direct or Coincidental Elimination of Stable Rotors or Focal Sources May Explain Successful Atrial Fibrillation Ablation: On-Treatment Analysis of the CONFIRM Trial (Conventional Ablation for AF With or Without Focal Impulse and Rotor Modulation)", Journal of the American College of Cardiology, vol. 62, No. 2, 2013, pp. 138-147.
Narayan et al., "Classifying Fractionated Electrograms in Human Atrial Fibrillation Using Monophasic Action Potentials and Activation Mapping: Evidence for Localized Drivers, Rate Acceleration and Non-Local Signal Etiologies", Heart Rhythm, vol. 8, No. 2, 2011, pp. 244-253.
Narayan et al., "Treatment of Atrial Fibrillation by the Ablation of Localized Sources: Confirm (Conventional Ablation or Atrial Fibrillation With or Without Focal Impulse and Rotor Modulation) Trial", Journal of the American College of Cardiology, vol. 60, No. 7, 2012, pp. 628-636.
Narayan et al., "Mechanistically based mapping of human cardiac fibrillation", The Journal of physiology, vol. 594, No. 9, 2016, pp. 2399-2415.
Narayan et al., "CrossTalk proposal: Rotors have been demonstrated to drive human atrial fibrillation", The Journal of physiology, vol. 592, No. 15, 2014, pp. 3163-6166.
Nattel, "New ideas about atrial fibrillation 50 years on", Nature, vol. 415, 2002, pp. 219-226.
Pandit et al., "Rotors and the Dynamics of Cardiac Fibrillation", Circulation research, vol. 112, No. 5, 2013, pp. 849-862.
Pappone et al., "Radiofrequency Catheter Ablation and Antiarrhythmic Drug Therapy: A Prospective, Randomized, 4-year Follow-Up Trial: The APAF study", Circ Arrhythm Electrophysiol, vol. 4, 2011, pp. 808-814.
Phlypo et al., Extraction of Atrial Activity from the ECG by Spectrally Constrained ICA Based on Kurtosis Sign, in International Conference on Independent Component Analysis and Signal Separation, pp. 641-648, 2007.
Pincus, "Approximate entropy (ApEn) as a complexity measure", Chaos, vol. 5, No. 1, 1995, pp. 110-117.
Richman et al., "Physiological time-series analysis using approximate entropy and sample entropy", American Journal of Physiology, Heart Circular of Physiology, vol. 278, pp. H2039-H2049, 2000.
Roberts et al., "Temporal and Spatial Complexity measures for EEG-based Brain—Computer Interfacing", Neural Systems Research Group, Department of Electrical & Electronic Engineering Imperial College of Science, Technology & Medicine, London, UK, 1998.
Rosso et al., "Wavelet entropy: a new tool for analysis of short duration brain electrical signals", Journal of Neuroscience Methods, vol. 105, 2001, pp. 65-75.
Salisbury et al., "Assessment of Chaotic Parameters in Nonstationary Electrocardiograms by Use of Empirical Mode Decomposition", Annals of biomedical engineering, 2004, vol. 32, No. 10, pp. 1348-1354.
Sasaki et al., "Localized rotors and focal impulse sources within the left atrium in human atrial fibrillation: A phase analysis of contact basket catheter electrograms", Journal of Arrhythmia, Apr. 30, 2016;32(2):141-144.
Schilling, "Analysis of Atrial Electrograms", KIT Scientific Publishing, vol. 17, 2012, 240 pages.
Schmitt et al., "Biatrial Multisite Mapping of Atrial Premature Complexes Triggering Onset of Atrial Fibrillation", Am J Cardiol (2002) 89:1381-1387.
Stavrakis et al., "The role of the autonomic ganglia in atrial fibrillation", JACC: Clinical Electrophysiology. Author manuscript, 2016, pp. 1-22.
Tzou et al., "Long-Term Outcome After Successful Catheter Ablation of Atrial Fibrillation", Circ Arrhythm Electrophysiol 2010;3:237-242.
Verma et al., "Approaches to Catheter Ablation for Persistent Atrial Fibrillation", New England Journal of Medicine, May 7, 2015;372(19):1812-22.
Weerasooriya et al., "Catheter Ablation for Atrial Fibrillation: Are Results Maintained at 5 years of Follow-Up?", Journal Df the American College of Cardiology, Jan. 11, 2011, vol. 52, No. 2, pp. 160-166.
Weiss et al., "The Dynamics of Cardiac Fibrillation", Circulation. Aug. 23, 2005;112(8)1232-40.
Wu et al., "Modified multiscale entropy for short-term time series analysis", Physica A 2013; 392(23):5865-5873.
Yamada et al., "Plasma brain natriuretic peptide level after radiofrequency catheter ablation of paroxysmal, persistent, and permanent atrial fibrillation", Europace Sep. 1, 2007;9(9):770-774.
Zaman et al., "Rotor mapping and ablation to treat atrial fibrillation", Current opinion in cardiology, Jan. 2015;30(1):24.
Zhao et al., "Atrial autonomic innervation remodelling and atrial fibrillation inducibility after epicardial ganglionic plexi ablation", Europace, Jun. 1, 2010;12(6):805-810.

(56) References Cited

OTHER PUBLICATIONS

Zlochiver et al., "Rotor Meandering Contributes to Irregularity in Electrograms during Atrial Fibrillation", Heart rhythm, Jun. 2008 ; 5(6):846-854.

* cited by examiner

GRAPHICALLY MAPPING ROTORS IN A HEART

CROSS-REFERENCE TO RELATED APPLICATION

The present application is based on and claims the benefit of U.S. provisional patent application Ser. No. 62/293,563, filed Feb. 10, 2016, and U.S. provisional patent application Ser. No. 62/296,418, filed Feb. 17, 2016. The entire content of the two aforesaid applications is hereby incorporated by reference.

FIELD

Embodiments of the present disclosure are directed to graphically indicating at least one location of a rotor or an aspect of a rotor in a heart using multi-scale frequency (MSF) calculations, kurtosis calculations, empirical mode decomposition (EMD) calculations, multi-scale entropy (MSE) calculations, and/or any combination thereof. For instance, some exemplary embodiments are directed to graphically indicating respective pivot points of rotors in a heart using any one or more of the aforesaid types of calculations.

BACKGROUND

Disclosed herein are techniques for rotor identification associated with atrial fibrillation (AF) or ventricular fibrillation (VF), such as to, for example, improve catheter ablation or pacing procedures in cardiac pacemakers.

Over two million people in the United States are currently afflicted with AF, which may be the most common sustained cardiac arrhythmia in humans, and many more cases are predicted in the near future. AF is also considered to be a cause of stroke.

Antiarrhythmic drugs are only partially effective and can cause serious side effects, including life-threatening arrhythmias. Despite great strides in understanding of AF, therapy using pharmacological, percutaneous and surgical interventional approaches remains suboptimal.

A limitation of therapy is the lack of mechanistic understanding for AF. However, it has recently been demonstrated that paroxysmal AF in patients is initiated by focal triggers localized usually to one of the pulmonary veins (PV) and can be remedied by a catheter-based ablation procedure. However, in persistent AF, the location of triggers is unclear; and therefore, therapy can be challenging. While advances have been made in ablating PV AF triggers in persistent and permanent forms of the arrhythmia, triggers may arise outside of PV, and extra-PV substrate plays an important role in arrhythmogenesis and maintenance of AF.

Catheter ablation is associated with limited success rates in patients with persistent AF. This may be the case because persistent AF is known to be at least partially caused by rotors, such as rotors located outside of the PV, and known mapping systems can predict locations of rotors outside of the PV in patients with persistent AF to some extent.

Known processing methods that are used to identify AF vulnerable regions of the heart include analysis of the dominant frequency (DF), complex fractionated electrograms (CFAE), phase analysis and local activation time (LAT) maps. These techniques can be based on temporal analysis of electrograms from different spatial locations of atria. However, the high frequency of recurrence of arrhythmias in patients with persistent AF after PV isolation and ablation shows that the current processing methods for AF analysis may not be adequate to predict critical areas of AF maintenance, such as locations of rotors. Also, known electro-anatomic mapping systems (such as ENSITE, NAVX, and CARTO) that employ known signal processing techniques (DF, CFAE, and LAT) may not be able to adequately predict a rotor's location outside of PV in patients with persistent AF. For example, the aforementioned mapping techniques may fail since clinical signals may not represent local activation. Also, virtual electrograms from non-contact methods may distort information in AF.

Data supports localized sources by reentrant mechanisms for AF showing that AF may be sustained by stable drivers such as electrical rotors. The pivot points of such rotor waves are believed to be good ablation targets to terminate AF in patients. About 77.8% success rate has been demonstrated by ablation of such sites in paroxysmal, persistent, and long-standing AF patients.

However, known mapping methods used for guiding catheter ablation, such as LAT maps and CFAE—mean index maps, have numerous limitations in their ability to accurately identify rotor pivot zones. This can be due to noise and misleading phase and activation times that distort these maps.

Thus, there are problems to be solved. For example, there is room for improvement with spatiotemporal mapping technology that can identify the rotor pivot points in a patient-specific manner.

SUMMARY

Embodiments of the present disclosure include methods for graphically indicating aspects of rotors (such as pivot points of rotors) associated with atrial or ventricular fibrillation. In some exemplary embodiments, the methods include receiving, using a processor, an electrogram for each of a plurality of spatial locations in a heart. Each of the electrograms can include time series data including a plurality of electrical potential readings over time.

In some exemplary embodiments, the methods also include generating, from the time series data, a dataset, the dataset including a plurality of values using a mathematical approach, wherein the mathematical approach is either a multi-scale frequency (MSF) approach, a kurtosis approach, an empirical mode decomposition (EMD) approach, or a multi-scale entropy (MSE) approach. Embodiments can also include graphically indicating pivot points of rotors associated with atrial or ventricular fibrillation according to the dataset.

Embodiments of graphically indicating pivot points of rotors can include generating, from the generated dataset, a map including a plurality of graphical indicators of the plurality of generated values at the plurality of spatial locations in the heart. In such examples, the map can include an image of the heart and a graphical indication of a location of a pivot point of a rotor in the heart. The plurality of graphical indicators of the plurality of values can include a range of different colors, shades of a gray or another color, different symbols, or indexed values each of the range corresponding to a value such that the displaying of the plurality of graphical indicators shows MSF levels, kurtosis levels, EMD levels, or MSE levels at different locations in the heart depending on the mathematical approach used. Also, the methods can include displaying the plurality of graphical indicators using a display device.

The methods can also include physically changing the heart at one or more of the plurality of spatial locations in the heart according to the generated dataset. The changing of the heart can include ablating the heart, such as through a catheter, at the one or more of the plurality of spatial locations in the heart, for example.

The methods can also include performing the plurality of electrograms at the plurality of spatial locations in the heart to obtain the time series data. The plurality of electrograms can be derived from an optical mapping experiment on the heart.

The dataset can also be a first dataset of a plurality of datasets, the plurality of values can be a first plurality of values of more than one set of values, and the mathematical approach can be a first mathematical approach of a plurality of approaches used in a process of graphically indicating aspects of rotors (such as pivot points of rotors) associated with atrial or ventricular fibrillation. Thus, for example, the methods can also include generating, from the time series data, a second dataset. The second dataset can include a second plurality of values using a second mathematical approach that is different from the first mathematical approach. The second mathematical approach can be a multi-scale frequency (MSF) approach, a kurtosis approach, an empirical mode decomposition (EMD) approach, or a multi-scale entropy (MSE) approach depending on the first mathematical approach used. Also, in such a case, the method can also include graphically indicating pivot points of rotors associated with atrial or ventricular fibrillation according to the second dataset.

Specifically, where the generating of the dataset uses the MSF approach, such a step can include generating, from the time series data, a dominant frequency (DF) dataset including a plurality of DF values corresponding to the plurality of spatial locations in the heart, and generating a multi-scale frequency index (i-MSF) using the DF dataset. Also, such a step can include generating an i-MSF dataset according to the DF dataset, wherein the i-MSF dataset includes a plurality of i-MSF values. The MSF approach can include using of band-pass quadrature filters. The MSF approach may also include use of a Hilbert transform operation to generate the i-MSF dataset by weighting various frequency components resulting from the filters. The MSF approach may also include use of multiple Log-Gabor filters. Also, in use of the MSF approach, respective center frequencies for the filters may be selected to span a physiological range of a heart rate. The MSF approach can also include using notch filters to remove harmonics of the DF dataset.

When the MSF approach uses Log-Gabor filters, the following equation can be used:

$$i\text{-MSF}=\rho_o[\Sigma_{i=1}^{N-1} q_i]^{-1}\Sigma_{i=1}^{N-1} 2^{i+0.5} q_{i+1},$$

wherein $q_i$ is an output of an ith Log-Gabor filter and $\rho_o$ is the center frequency of the first Log-Gabor filter. The Log-Gabor filters can include a one-dimensional Log-Gabor function with a frequency response provided by the following equation:

$$G(f) = \exp\left(\frac{-(\log(f/f_0))^2}{2(\log(\sigma/f_0))^2}\right),$$

wherein $f_0$ is the center frequency and a is related to bandwidth (B). To maintain a same shape while the frequency parameter is varied, the ratio can be configured to remain constant. Alternatively, the Log-Gabor filters can include a one-dimensional Log-Gabor function with a modified frequency response provided by the following equation:

$$G(f) = \frac{f_0}{f}\exp\left(\frac{-(\log(f/f_0))^2}{2(\log(\sigma/f_0))^2}\right),$$

wherein $f_0$ is the center frequency and a is related to bandwidth (B), and wherein $B=2\sqrt{2/\log(2)} \, (\|\log(\sigma_f/f_0)\|)$. In this alternative embodiment, to maintain a same shape while the frequency parameter is varied, the ratio $\sigma/f_0$ can be configured to remain constant. In yet another alternative, the Log-Gabor filters include a two-dimensional Log-Gabor function with a frequency response provided by the following equation:

$$G(f, \theta) = \exp\left(\frac{-(\log(f/f_0))^2}{2(\log(\sigma_f/f_0))^2}\right)\exp\left(\frac{-(\theta - \theta_0)^2}{2\sigma_\theta^2}\right),$$

wherein $f_0$ is the center frequency, $\sigma_f$ is the width parameter related to bandwidth (B) for the frequency, $\theta_0$ is the center orientation, and $\sigma_\theta$
is the width parameter related to bandwidth (B) of the orientation, $B=2\sqrt{2/\log(2)}(\|\log(\sigma_f/f_0)\|)$ and $B_\theta=2\sigma\sqrt{2\log 2}$.

Specifically, where the generating of the dataset uses the kurtosis approach, such a step can include generating, from the time series data, a probability density function (PDF); and generating, from the PDF, a kurtosis dataset. The kurtosis approach can include generating a kurtosis value or a value related to the fourth central moment of the PDF. The kurtosis value or the value related to the fourth central moment can be determined using the following equation:

$$Kurt(X) = E\left\{\left[\frac{X - E\{X\}}{\sigma}\right]^4\right\} = \frac{\mu_X^4}{\sigma_X^4},$$

wherein x represents the time series data, wherein μ is the central moment and $\mu^4$ is the fourth central moment, σ is the standard deviation, E is the expectation value or mean of a stochastic variable X, as determined by using the following equation:
wherein f(x) is the PDF.

$$E\{X\} = \int_{-\infty}^{\infty} x \cdot f(x)dx = \mu_X$$

Specifically, where the generating of the dataset uses the EMD approach, such a step can include generating, from the time series data, an intrinsic mode functions index (i-IMF) dataset, the i-IMF dataset including a plurality of intrinsic mode function (IMF) values. For each IMF value, the approach can include computing a moving-averaged time series for a selected time scale factor. The computing the moving-averaged time series for a selected time scale factor can use the following equation:

$$Z_j^\tau = \frac{1}{(\tau)}\sum_{i=j}^{\tau+j-1} X_i,$$

where $1 \leq j \leq N_{-\tau}$ and i=1, 2, 3, N, wherein $Z_j^\tau$ is the moving-averaged time series, $\tau$ is the selected time scale factor, and $x=\{x_1, x_2, x_3 \ldots x_N\}$ represents the time series data of length N.

In such exemplary embodiments, the IMF values can be measured using the MSE approach. An MSE value for the second, third, and fourth IMF value can be computed using the MSE approach using a time scale factor of two. Each IMF value can be computed as an average MSE value of the second, third, and fourth IMF values.

Specifically, where the generating of the dataset uses the MSE approach, such a step can include generating, from the time series data, a MSE dataset that includes a plurality of MSE values. Also, the generating of the MSE dataset can include: (i) generating, from the time series data, a nearest neighbor moving-averaged time series for a selected time scale factor that accounts for past and future time series values while computing a nearest neighbor average; (ii) generating, from the nearest neighbor moving-averaged time series, template vectors with a dimension and a delay; (iii) generating, from the template vectors, a Euclidean distance for each pair of template vectors, wherein the template vectors include pairs of template vectors; (iv) matching corresponding template vector pairs from the template vectors based on a pre-defined tolerance threshold; and (v) repeating processes (i)-(iv) for a certain number of dimensions. The generating of a nearest neighbor moving-averaged time series can include using the following equation:

$$Z_j^\tau = \frac{1}{(2\tau+1)} \sum_{i=j}^{2\tau+1} X_i,$$

where $1 \leq j \leq N_{-\tau}$ and i=1, 2, 3, . . . N, and wherein $Z_{j\tau}$ is the nearest neighbor moving-averaged time series, $\tau$ is the selected time scale factor, and $x=\{x_1, x_2, x_3 \ldots x_N\}$ represents the time series data of length N. The generating template vectors uses the following equation:

$$y_k^m(\delta) = \{Z_k Z_{k+\delta} \ldots Z_{k+(m-1)\delta}\},$$

where $1 \leq k \leq N_{-m\delta}$, wherein $y_k^m(\delta)$ is the template vectors with dimension m and delay $\delta$. The generating of a Euclidean distance can include using an infinity norm operation, and can use the following equation:

$$d_{ij}^m(\delta) = \|y_i^m(\delta) - y_j^m(\delta)\|_\infty,$$

where $1 \leq i, j \leq N_{-m\delta}$, and $j > i+\delta$; wherein the Euclidean distance is $d_{ij}^m$, and each pair of template vectors is $\{y_i^m, y_j^m\}$. The matching of corresponding template vector pairs can use the following equation: $d_{ij}^m(\delta) \leq r$, and wherein r is the pre-defined tolerance threshold. The certain number of dimensions can be m+1 dimensions. The MSE approach can also include determining a total number of matched template vectors. The generating of an MSE value of the MSE dataset can use the following equation:

$$MSE(x, m, \delta, r) = -\ln \frac{n(m+1, \delta, r)}{n(m, \delta, r)},$$

wherein n(m+1, $\delta$, r) is the total number of matched template vectors.

Also, in some exemplary embodiments, at least some of the operations of the methods can be implemented by computer executable instructions stored on a non-transitory computer readable medium. For example, some embodiments can include a computer processor and a non-transitory computer readable medium readable by the computer processor. An exemplary non-transitory computer readable medium can include instructions executable by the processor to receive an electrogram for each of a plurality of spatial locations in a heart, each electrogram comprising time series data including a plurality of electrical potential readings over time; instructions executable by the processor to generate, from the time series data, a dataset, the dataset including a plurality of values using a mathematical approach, wherein the mathematical approach is either a multi-scale frequency (MSF) approach, a kurtosis approach, an empirical mode decomposition (EMD) approach, or a multi-scale entropy (MSE) approach; and instructions executable by the processor to graphically indicate pivot points of rotors associated with atrial or ventricular fibrillation according to the dataset.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the Background.

BRIEF DESCRIPTION OF THE DRAWINGS

FIG. 11 illustrates corresponding amplitude plots.

FIG. 14 illustrates a corresponding histogram showing the kurtosis value associated with the optical data at the approximate pixel location near the pivot point.

FIG. 15 illustrates a corresponding histogram showing the kurtosis value associated with the optical data at the pixel location in the periphery.

DETAILED DESCRIPTION OF ILLUSTRATIVE EMBODIMENTS

Figure 1:
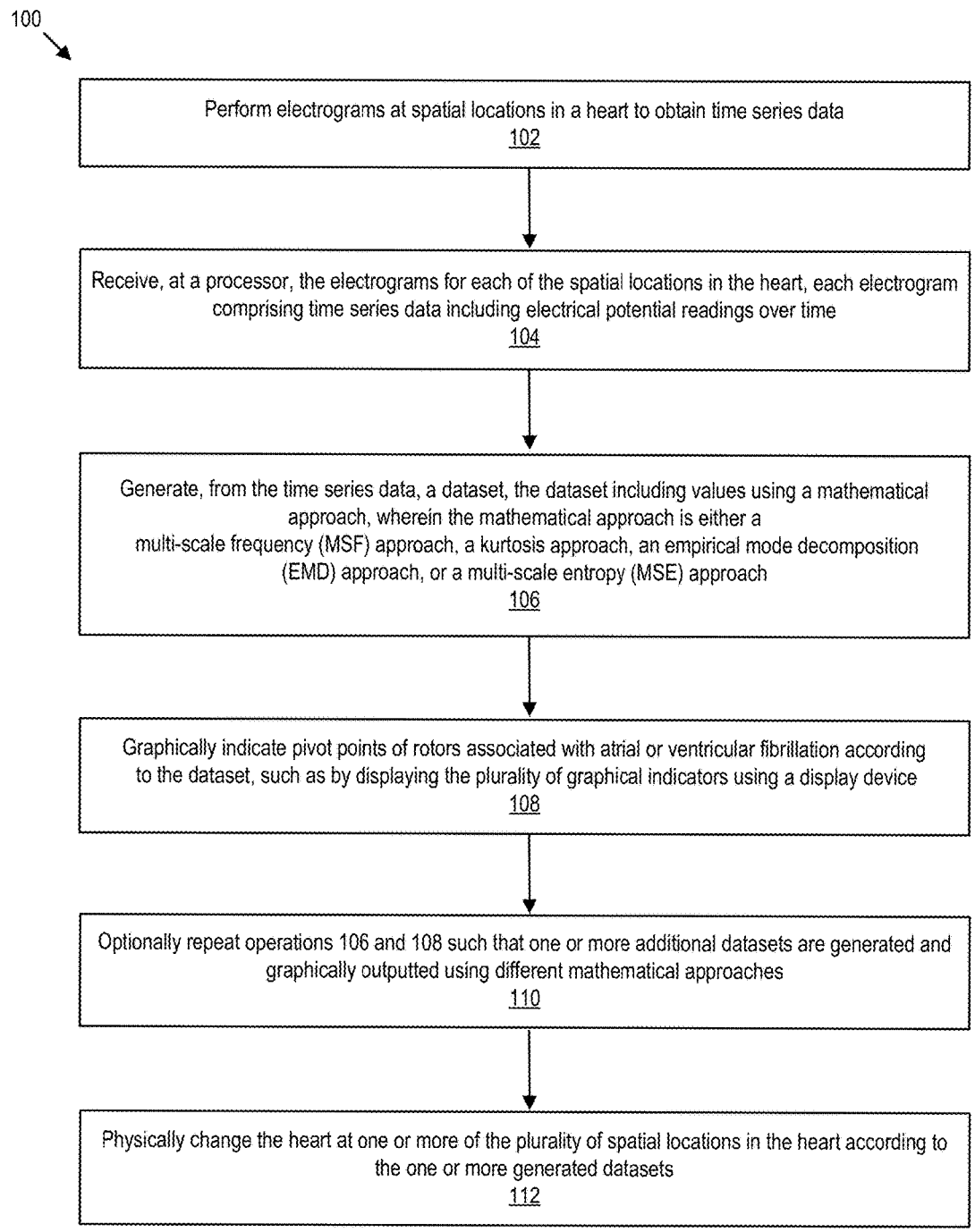
FIG. 1 illustrates exemplary operations performed by a system that can implement rotor identification in a fibrillation, such as an atrial fibrillation, using multi-scale frequency (MSF) calculations, kurtosis calculations, empirical mode decomposition (EMD) calculations, multi-scale entropy (MSE) calculations, or any combination thereof.

Embodiments of the present disclosure are described more fully hereinafter with reference to the accompanying drawings. Elements that are identified using the same or similar reference characters refer to the same or similar elements. The various embodiments of the present disclosure may, however, be embodied in many different forms and the invention should not be construed as limited to only the embodiments set forth herein.

Specific details are given in the following description to provide a thorough understanding of the embodiments. However, it is understood by those of ordinary skill in the art that the embodiments may be practiced without these specific details. For example, circuits, systems, networks, processes, frames, supports, connectors, motors, processors, and other components may not be shown, or shown in block diagram form in order to not obscure the embodiments in unnecessary detail.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present disclosure.

Unless otherwise defined, all terms (including technical and scientific terms) used herein have the same meaning as commonly understood by one of ordinary skill in the art to which this present disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will further be appreciated by one of skill in the art, embodiments of the present disclosure may be embodied as methods, systems, devices, and/or computer program products, for example. Accordingly, embodiments of the present disclosure may take the form of an entirely hardware embodiment, an entirely software embodiment or an embodiment combining software and hardware aspects. The computer program or software aspect of embodiments of the present disclosure may comprise computer readable instructions or code stored in a computer readable medium or memory. Execution of the program instructions by one or more processors (e.g., central processing unit) results in the one or more processors performing one or more functions or method steps described herein. Any suitable patent subject matter eligible computer readable media or memory may be utilized including, for example, hard disks, CD-ROMs, optical storage devices, or magnetic storage devices. Such computer readable media or memory do not include transitory waves or signals.

Computer program or software aspects of embodiments of the present disclosure may comprise computer readable instructions or code stored in a computer readable medium or memory. Execution of the program instructions by one or more processors (e.g., central processing unit) results in the one or more processors performing one or more functions or method steps described herein. Any suitable patent subject matter eligible computer readable media or memory may be utilized including, for example, hard disks, CD-ROMs, optical storage devices, or magnetic storage devices. Such computer readable media or memory do not include transitory waves or signals.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure may also be described using flowchart illustrations and block diagrams. Although a flowchart or block diagram may describe the operations as a sequential process, many of the operations can be performed in parallel or concurrently. In addition, the order of the operations may be re-arranged. In addition, the order of the operations may be re-arranged. Embodiments of methods described herein include not preforming individual method steps and embodiments described herein. A process is terminated when its operations are completed, but could have additional steps not included in a figure or described herein.

It is understood that one or more of the blocks (of the flowcharts and block diagrams) may be implemented by computer program instructions. These program instructions may be provided to a processor circuit, such as a microprocessor, microcontroller or other processor, which executes the instructions to implement the functions specified in the block or blocks through a series of operational steps to be performed by the processor(s) and corresponding hardware components.

Also, although the present disclosure is described with reference to preferred embodiments, workers skilled in the art will recognize that changes may be made in form and detail without departing from the spirit and scope of the present disclosure.

Overview

Disclosed herein are embodiments of multiple mathematical approaches for identifying regions of rotors associated with AF or VF. Such techniques can produce patient-specific dynamic spatiotemporal maps of active substrates during AF or VF (such as during persistent AF). These maps can provide information during an electrophysiology study to provide guidance for patient tailored ablation therapy. Also, these techniques can overcome limitations with known mapping systems.

In examples described herein, multi-scale frequency (MSF), kurtosis, empirical mode decomposition (EMD), multi-scale entropy (MSE) calculations and/or mapping may be used to overcome limitations in conventional mapping techniques. For example, there are limitations with using a Fourier transform to calculate the DF, alone. For instance, such a technique is limited in facilitating identification the rotor pivot point. It appears that the chaotic nature of the rotor at the pivot point yields various frequency components. This is why, for example, the MSF approach described herein can provide an improvement to identifying the rotor pivot point or another indicator part of the rotor by using the various frequency components to yield information regarding the indicator part, which may include the location and identification of the indicator part. Values from respective datasets resulting from the calculations of the MSF approach and the other approaches emphasized herein can be used to identify rotor cores and to produce patient-specific dynamic spatiotemporal maps of AF active substrates for patient-tailored ablation therapy.

The techniques disclosed herein, which use calculated MSF levels, kurtosis levels, EMD levels, or MSE levels, can be used individually or in combination. Also, they can be used for identification of self-sustaining regions of chaotic rhythms in AF or VF.

The term entropy used herein is the amount of disorder of a system or a part of a system.

In one example, entropy includes the measure of information based on symbolic dynamics, which can reflect different intrinsic dynamics of different time series. This is different from the time domain and frequency domain analysis of DF, CFAE, or LAT, for example, where such dynamics are not used. Also, due to meandering of a rotor in time and space, frequency distribution of a part of the rotor, such as at a pivot point of the rotor, can be complex, and not easily to be captured by DF.

The term kurtosis used herein is a measure of "tailedness" of a probability distribution of a real-valued random variable. In a similar way to the concept of skewness, kurtosis is a descriptor of the shape of a probability distribution and, just as for skewness, there are different ways of quantifying it for a theoretical distribution and corresponding ways of estimating it from a sample. An exemplary measure of kurtosis can be based on a scaled version of the fourth moment of given data. This number measures heavy tails or "peakedness". For this measure, higher kurtosis means more of the variance is the result of infrequent extreme deviations, as opposed to frequent smaller sized deviations. The kurtosis is the fourth standardized moment, defined as:

$$Kurt[X] = \frac{\mu_4}{\sigma^4} = \frac{E[(X-\mu)^4]}{(E[(X-\mu)^2])^2},$$

where μ4 is the fourth central moment and σ is the standard deviation.

The symbolic dynamics approach can include binning electrograms or electrical potential readings over time according to amplitude, which can result in a plurality of bins per electrogram. Each bin of the plurality of bins can represent an amplitude or amplitude range of the electrical potential readings and include a frequency of occurrences of the amplitude or amplitude range of the electrical potential readings. Then, the bins may be displayed as a histogram. A probability density of each bin of the plurality of bins can be determined per electrogram. This data (including symbols of the histogram for example) can then be analyzed and/or processed using entropy calculations, such as MSE calculations. A MSE value can be calculated based on the determined probability densities, per electrogram. Also, values derived from the multi-scale frequency (MSF), kurtosis, empirical mode decomposition (EMD) calculations can be based on the determined probability densities, per electrogram. The symbolic dynamics approach can be used by each of the approaches described herein, even though the operations for the symbolic dynamics approach is not shown with the operations depicted in FIGS. 7, 16, and 23 for the MSF, EMD, and MSE approaches respectively. The symbolic dynamics approach has not been shown in FIGS. 7, 16, and 23 so that the figures can focus on the unique operations of the MSF, EMD, and MSE approaches respectively.

FIG. 1 illustrates exemplary operations 100 performed by a system that can implement rotor identification in a fibrillation, such as atrial or ventricular fibrillation, and treat the fibrillation accordingly. Operations 100 form a method for identifying and treating a pivot point or some other aspect of a rotor in a fibrillation (such as an atrial or ventricular fibrillation). The operations 100 include performing electrograms such as those derived from an optical mapping experiment feasible on human or animal hearts, including any in vivo or in vitro experiment to obtain time series data, at 102. The time series data may be of a plurality of electrograms or a plurality of electrical potential readings captured in the experiment. In other words, at operation 102, the system can perform electrograms at spatial locations in a heart to obtain time series data, and the electrograms can be derived from an optical mapping experiment on the heart.

The electrograms or electrical potential readings at different locations of the heart over time may be obtained through an optical mapping of the heart. In some embodiments, the optical mapping of the heart involves mapping through optics experiments. The time series data of the plurality of electrograms or the plurality of electrical potential readings can be obtained from any optical mapping experiments feasible on human or animal hearts, including any in vivo or in vitro experiment.

For example, an optical mapping experiment can include a heart put through an in vitro experiment such as a Langendorff heart assay or an in vivo assay similar to the Langendorff heart assay that does not remove the heart from the organism. In one example, a certain amount of voltage-sensitive dye, such as di-4-ANEPPS (5 μg/mL), can be added to the perfusate. After staining with the dye, a laser, such as a 532-nm green laser, can be used to illuminate a part of the heart including the perfusate, such as an epicardial surface of the heart. From the illumination, visible or invisible radiation illuminated from the heart can captured with one or more sensors or cameras. For instance, fluorescence intensity can be captured with two 12-bit CCD cameras, which run at 1000 frames per second with 64×64 pixel resolution. An atrial or ventricular tachycardia can be induced on the heart (such as via burst pacing), and recordings of images, such as phase movies, can be obtained at parts of the heart having or expected to have rotors. The recording of images can be processed as described herein, such as by using any one or more of the approaches and calculations described herein.

Figure 3:
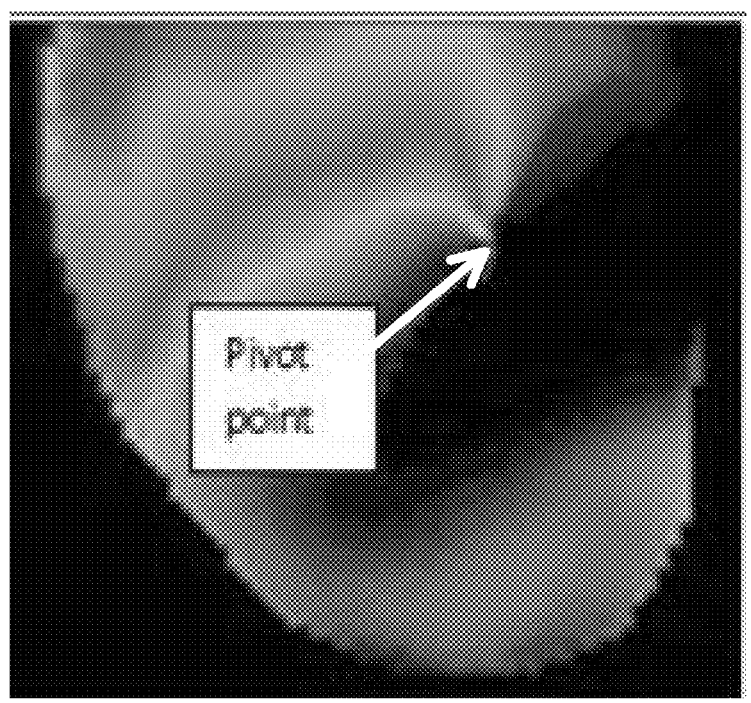
FIG. 3 illustrates exemplary graphics identifying a rotor using a phase movie from an optical mapping animal experiment.

FIG. 3 illustrates an example of a single rotor in an isolated rabbit heart from optical mapping experiments. In FIG. 3, the pivot point of the rotor is indicated by an arrow. FIG. 3 is an exemplary snapshot of a phase movie, where different colors represent different phases of action potential. The convergence of different phases may correspond to a singularity point, e.g., the pivotal point or core of the rotor, which can be identified by the arrow.

Also, for example, an electrophysiological study can be done in vivo, such as with a patient in a postabsorptive state under general anesthesia. A part of the heart, such as the left atrium, can be accessed, such as accessed transseptally. In such experiments, a blood clotting treatment, such as a single bolus of 100 IU/kg heparin, can be administered and repeated to maintain activated clotting, such as for time above 190 seconds. Electro-anatomic mapping, such as fluoroscopy, can be performed. For instance, a CARTO mapping system (such as a Biosense-Webster mapping system) can be used. In such examples, the CARTO mapping system can have a sensor position accuracy of 0.8 mm and 5°. Also, a catheter combined with a fluoroscopy sensor, such as the CARTO mapping system, can sense the 2D or 3D geometry of the part of the heart, such as a chamber of the left atrium. Reconstruction of the part of the heart virtually can be done in real time. Also, a recording system, used in the mapping, can, at different spatial locations of the heart, record the plurality of electrograms or the plurality of electrical potential readings such as from one of the sensors mentioned herein. For instance, at each point of recording, a system, such as the CARTO mapping system, can record electrograms, such as 12-lead ECG and unipolar and bipolar intracardiac electrograms sampled at 977 Hz, thus allowing the electrophysiological information to be encoded, such as color coded, and superimposed on the anatomic map. Also, evenly distributed points can be recorded such as by using a fill threshold of 20 mm throughout the right atrium, left atrium, and any other pertinent part of the heart. At each point, electrograms, such as 5-15 second electrograms, together with the surface ECG, can be acquired. Endocardial contact during point acquisition can be facilitated by fluoroscopic visualization of catheter motion, the distance to geometry signaled by the catheter icon on the CARTO system, and/or in a subset with intracardiac echocardiography. A high-resolution sensing catheter, such as a high resolution PENTARAY NAV catheter, can be used in a sequential scanning approach to fully map the relevant parts of the heart, such as both atrial chambers. The raw electrograms can be filtered, such as by a bandpass filter at 30-500 Hz. They can also be exported for offline processing. The raw electrograms can exported offline and processed using software or firmware, such as custom written MATLAB software, to obtain MSF, kurtosis, EMD, and MSE datasets. Finally, any of the electrograms or datasets described herein can be superimposed on the anatomic map of the heart to obtain a respective 2D or 3D map.

In some exemplary embodiments, time series data can be obtained from pre-filtered intra-atrial electrograms such as obtained from a Prucka system. These intra-atrial electrograms can be free from high frequency noise. A notch filter, such as a 60 Hz notch filter, can be used to remove noise such as line noise contamination. The electrograms can be visually inspected for ventricular far field (VFF) noise and can be verified to have minimal or no VFF contamination. Instructions, such as software or firmware based instructions like a custom MATLAB program, can be used to do the data processing described herein. Also, such electrograms can be used to compute the MSF, kurtosis, EMD, and MSE values described herein.

Referring back to FIG. 1, the operations 100 include receiving, by a processor (such as CPU 402 illustrated in FIG. 4), at 104, the electrograms for each of the spatial locations in the heart, each electrogram comprising time series data including electrical potential readings over time. In other words, the time series data obtained from a plurality of electrograms or electrical potential readings of a heart are received. As mentioned herein, the electrograms can be derived from electrical potential readings, such as those described herein. In instances using electrograms, each electrogram of the plurality of electrograms corresponds to a different spatial location (such as a different unique spatial location) in the heart and each electrogram of the plurality of electrograms includes a plurality of electrical potential readings over a time series. These readings may be voltage readings (such as shown by chart 502a of FIG. 5). Also, different locations in the heart are represented by respective sets of data.

Additionally, at 104 (not depicted in FIG. 1), the processor may generate histograms using the sets of data and the symbolic dynamics approach disclosed herein. The symbolic dynamics approach may include binning each electrogram of the plurality of electrograms (such as binning each set of electrical potentials) according to amplitude, which results in a plurality of bins per electrogram. Each bin of the plurality of bins represents an amplitude or amplitude range of the electrical potentials and includes a frequency of occurrences of the amplitude or amplitude range. Also, not depicted in FIG. 1, the bins may be displayed as a histogram, such as shown by histogram 502b of FIG. 5. The operation at 104 may also include determining a probability density of each bin of the plurality of bins, per electrogram (which is also not shown in FIG. 1). The histogram may also be displayed after the determination of the probability densities.

At 106, the processor can generate, from the time series data, a dataset, the dataset including values using a mathematical approach, wherein the mathematical approach is either a multi-scale frequency (MSF) approach, a kurtosis approach, an empirical mode decomposition (EMD) approach, or a multi-scale entropy (MSE) approach. In some examples, using such approaches, the processor can analyze and/or process symbols in a histogram derived from the symbolic dynamics approach. Operation 106 may include determining an MSF, kurtosis, EMD or MSE value or level according to the determined probability densities, per electrogram.

At 108, the processor facilitates graphically indicating pivot points of rotors associated with atrial or ventricular fibrillation according to the generated dataset generated at operation 106. For example, the operation 108 can include displaying the plurality of graphical indicators using a display device. The graphically indicating of pivot points of rotors can also include generating, from the generated dataset, a map including graphical indicators of the generated values at the spatial locations in the heart, and the map can include an image of the heart and a graphical indication of a location of a pivot point of a rotor in the heart. The graphical indicators of the values can include a range of different colors, shades of a gray or another color, different symbols, or indexed values each of the range corresponding to a value such that the displaying of the graphical indicators shows MSF levels, kurtosis levels, EMD levels, or MSE levels at different locations in the heart depending on the mathematical approach used.

At 110, operations at 106 and 108 can be repeated, such that at least a second generated dataset in addition to the first generated dataset occurs, a second set of values in addition to the first set of values occurs, and a second mathematical approach in addition to the first mathematical approach is used. In other words, at 110, the processor can further generate, from the time series data, a second dataset, the second dataset including a second plurality of values using a second mathematical approach that is different from the first mathematical approach, wherein the second mathematical approach is either a multi-scale frequency (MSF) approach, a kurtosis approach, an empirical mode decomposition (EMD) approach, or a multi-scale entropy (MSE) approach depending on the first mathematical approach used. And, then the processor can graphically indicate pivot points of rotors associated with atrial or ventricular fibrillation according to the second dataset as well and so on.

At 112, the heart can be physically changed at one or more of the plurality of spatial locations in the heart according to the one or more generated datasets, such as the first and second datasets. The changing of the heart can include a physical treatment of the heart, such as ablating portions of the heart at the one or more of the plurality of spatial locations in the heart, for example.

In an exemplary embodiment, the methods disclosed herein can use a symbolic dynamics approach that is based on if fluctuations of two or more time series are governed by different underlying dynamics then the derivations of corresponding symbolic sequences are not related. Histograms of resulting symbolic sequences can give a reconstruction of the sequences respective histories and provide a visual representation of intrinsic dynamic patterns. These intrinsic dynamics can be ignored in the time domain and frequency domain analysis, which can be the basis for existing signal processing techniques for rotor identification.

The process of symbolization can be used to represent any possible variation over time, depending on the number of symbols (such as amplitude bins) and the sequence lengths used. Thus, such symbolic dynamics can be independent of any assumptions about the nature of the signals. Symbolic dynamics approach can be applied to time series data obtained from the experiments disclosed herein to generate the histograms.

Symbols can be created by amplitude bins and the information content of these symbols can be captured by the different approaches described herein, such as the kurtosis approach for example. The values generated in the operations 100 can also be a statistical measure of information content that can be based on the distribution of amplitude values within a signal histogram for example.

The spatial uncertainty of wave front direction in a part of a rotor, such as the pivot zone or point of a rotor, can lead to information uncertainty in a bipolar electrogram from that part. For instance, the changing wave front direction near the pivot zone or point may cause a broader distribution in the bipolar voltage histogram. This may cause a pivot point or zone to have a higher MSF, kurtosis, EMD or MSE level when compared to signals from the periphery of the rotor.

Such values or levels can represent the distribution of signal values from electrograms within the histogram. Each electrogram from different spatial location can be binned, such as by using a bin size of 0.001 mV, according to its amplitude into a voltage histogram. Then, the relative probability density 'p' may be defined, such as according to the number of counts in an amplitude bin divided by the sum of bin counts in all the bins. MSF, kurtosis, EMD or MSE values can be calculated for the intra-atrial electrograms or other types of datasets using mathematical approaches disclosed herein that use the results of the symbolic dynamics approach.

The derived values and levels generated in operations 100 can be used to generate a 2D or 3D map depending on the implementation. The map can then be displayed via a display device. The map can continuously update itself as new time series data is inputted into the system or as the analysis of symbols reoccurs.

In an example, the aforementioned maps can be generated by using the calculated values, such as from MATLAB, and re-annotating them exactly to the carto points (such as by using the GE Prucka system from which the raw intra-atrial electrograms were obtained). This can be accomplished manually or automatically. Subsequent to such annotation, the annotated data can then be superimposed on the anatomical map to obtain a full 3D distribution in the atria by interpolation between the CARTO points for visualization and color coded to represent the range of MSF, kurtosis, EMD or MSE values. The estimated values can be multiplied by a factor (such as by a factor of 10) for display purposes. The CARTO software also allows 3D viewing of a 3D map for visualization and interpretation to identify potential active sites that may cause and maintain AF.

As mentioned herein, FIG. 3 illustrates an example of a single rotor in an isolated rabbit heart from optical mapping experiments. In FIG. 3, the pivot point of the rotor is indicated by an arrow. FIG. 3 is an exemplary snapshot of a phase movie, where different colors represent different phases of action potential. The convergence of different phases may correspond to a singularity point, e.g., the pivotal point or core of the rotor, which can be identified by the arrow. FIGS. 8, 9, 12, 13, 19-20, and 25-27 show exemplary 2D maps calculated for the same rotor illustrated in FIG. 3. In these figures, the DF, MSF, kurtosis, EMD or MSE values may be normalized to a maximum value for better visualization.

Figure 5:
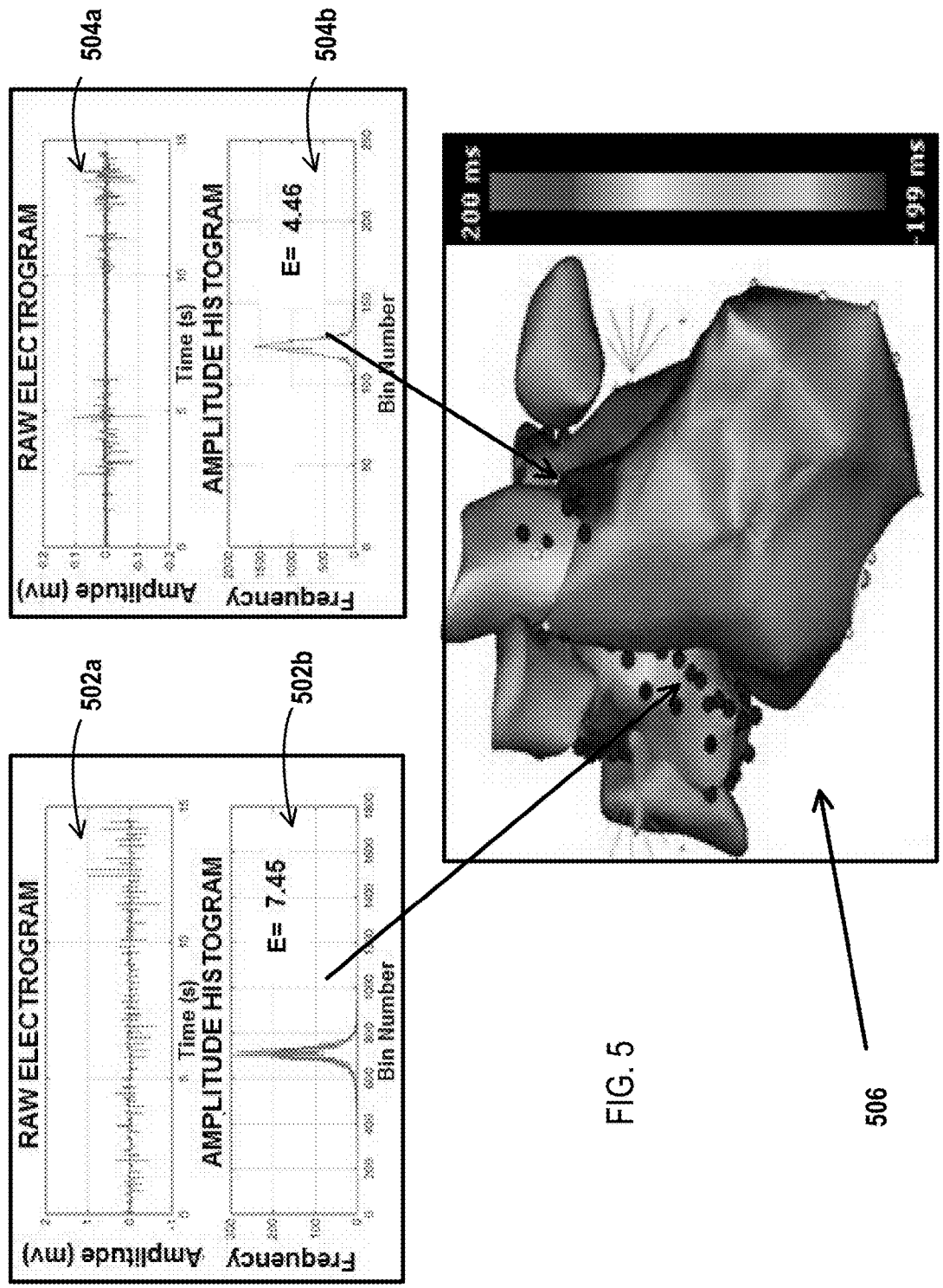
FIG. 5 illustrates examples of raw electrograms, amplitude histograms, and a 3D distribution of a LAT from a CARTO system.

FIG. 5 illustrates raw intra-atrial electrogram charts 502a and 504a from a carto point in LA, amplitude histograms 502b and 504b of the corresponding electrograms, and corresponding entropy values to provide an example of the benefit of such electrograms. Also shown, is an image 506 of distribution of LAT in the right anterior oblique (RAO) views obtained from a CARTO system.

Figure 6:
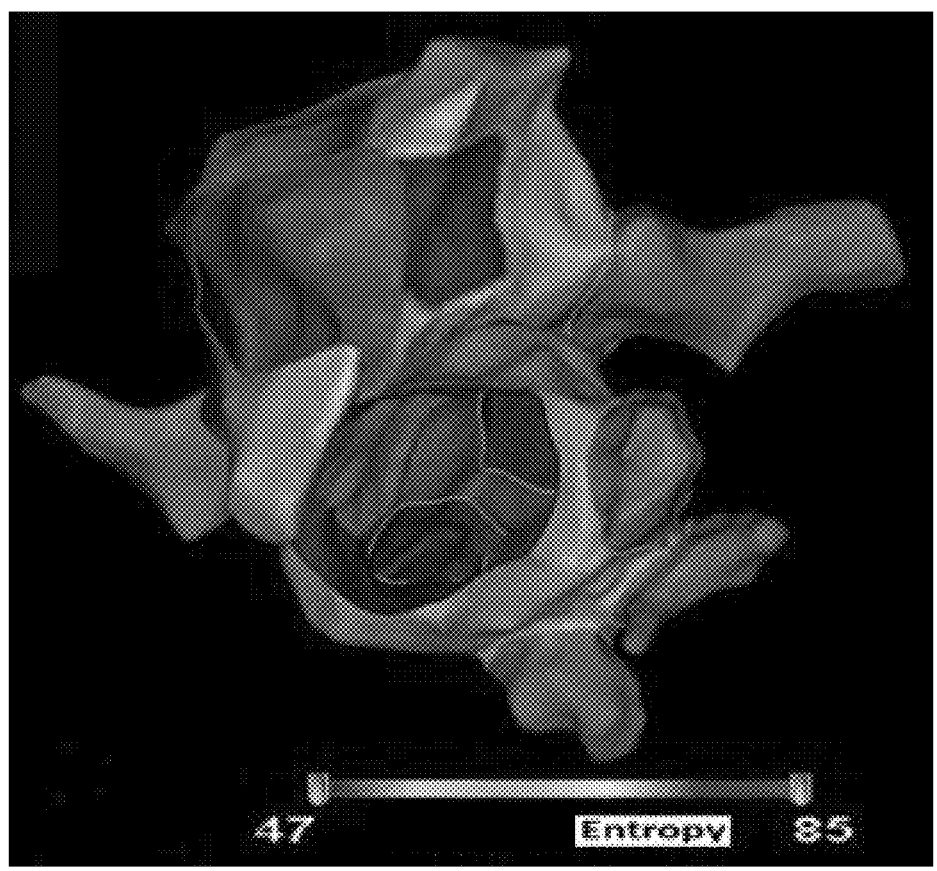
FIG. 6 illustrates an example of 3D distribution of entropy values in a heart having persistent AF. Higher values of entropy might show the region of a rotor.

FIG. 6 illustrates a 3D entropy distribution of the atria showing higher regions at the base of right atrial appendage. Note that for visualization purposes, entropy was multiplied by 10. Similar techniques can be applied to the other mathematical approaches described herein.

In examples, the symbolic dynamic approach can be used to develop a more robust spatiotemporal mapping system using entropy to address the inherent limitations of other approaches for mapping. MSF, kurtosis, EMD and MSE approaches using the optical mapping data with known rotor pivot zones can demonstrate feasibility to accurately identify rotor core area. Results of applying such validated approaches to human persistent AF data may show that such mathematical results provide differentiable areas which have lower and higher values or levels. These results can be superimposed directly on a 2D or 3D anatomical map provided direct visualization of an anatomically accurate 2D or 3D MSF, kurtosis, EMD or MSE map.

Higher levels in the MSF, kurtosis, EMD and MSE datasets can be at the base of the right atrial appendage which could indicate the presence of active AF causing sites, which is outside the PV area. Although a causal relationship has not been established, it can be inferred that for persistent AF patients the active triggers that cause AF may arise from outside PV regions explaining why conventional ablation strategies targeting PV area have failed in the past.

An Exemplary Combined Approach

Figure 2:
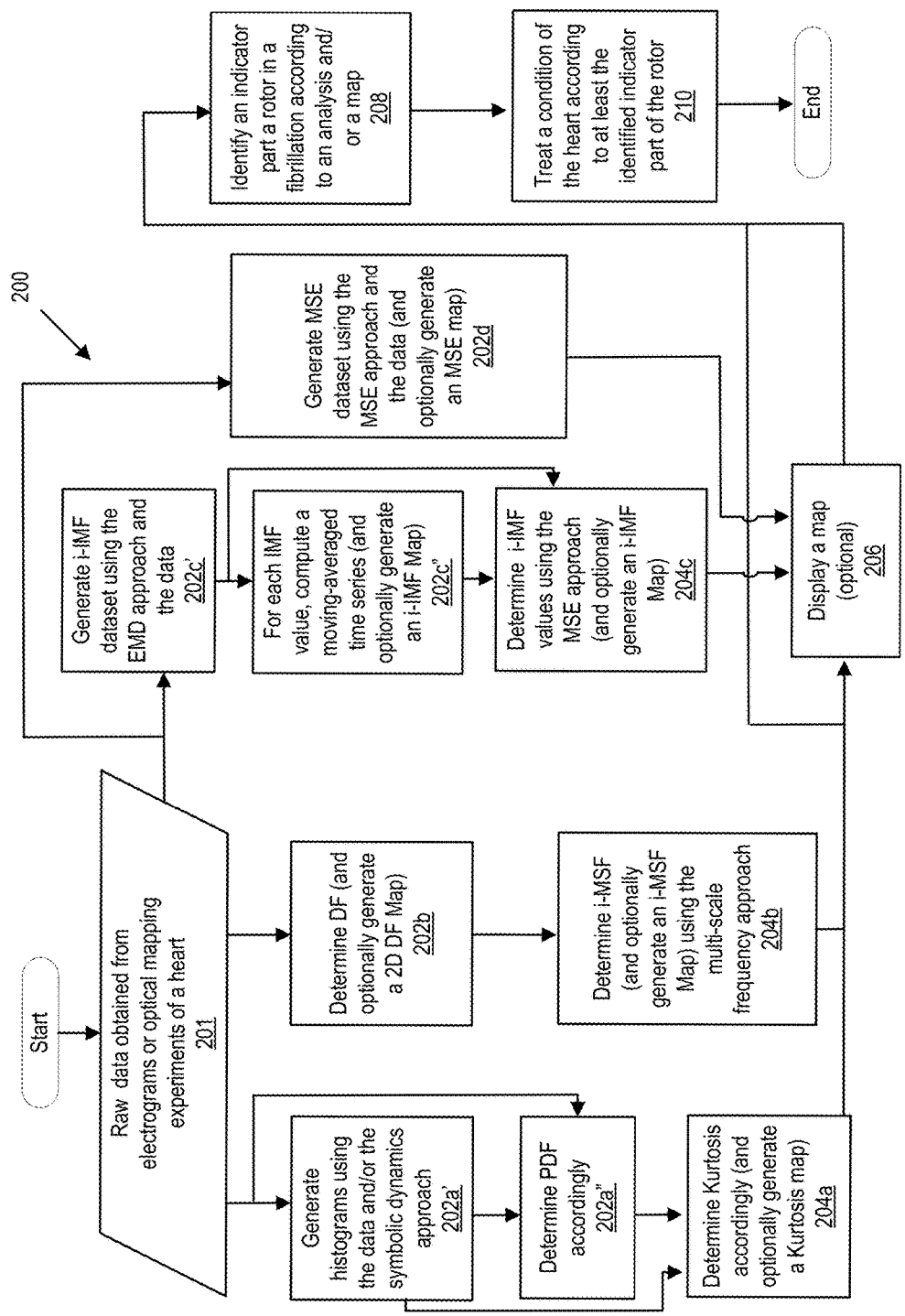
FIG. 2 illustrates exemplary operations performed by a system that can implement rotor identification in a fibrillation, such as an atrial fibrillation, using MSF calculations, kurtosis calculations, EMD calculations, MSE calculations, or any combination thereof.

FIG. 2 illustrates exemplary operations 200 performed by a system that can implement rotor identification in a fibrillation, such as an atrial fibrillation, using MSF calculations, kurtosis calculations, EMD calculations, MSE calculations, or any combination thereof.

Operations 200 form a method for identifying an indicator part of a rotor in a fibrillation, such as a pivot point or some other aspect of a rotor that can at least partially indicate an existence of a rotor. The operations 200 include receiving, by a processor, raw data 201 obtained from a plurality of electrograms or optical mapping experiments of a heart. In some examples, the raw data 201 may be time series data.

In examples using optical mapping experiments, optical mapping recordings may be achieved by adding a voltage-sensitive dye to a perfusate added or within the heart. After staining, a selective emission of light (such as a laser) may illuminate an epicardial surface of the heart. Upon illumination, fluorescence intensity can be captured in optical mapping recordings, such as by CCD cameras. From the optical mapping recordings, phase movies of rotors on the heart can be generated by the system. A phase movie can correspond to a unique spatial location of the heart, and a snapshot of a phase movie can be generated (such as shown in FIG. 3). The raw data 201 can then be retrieve from a phase movie or a snapshot of the phase movie.

Figure 11:
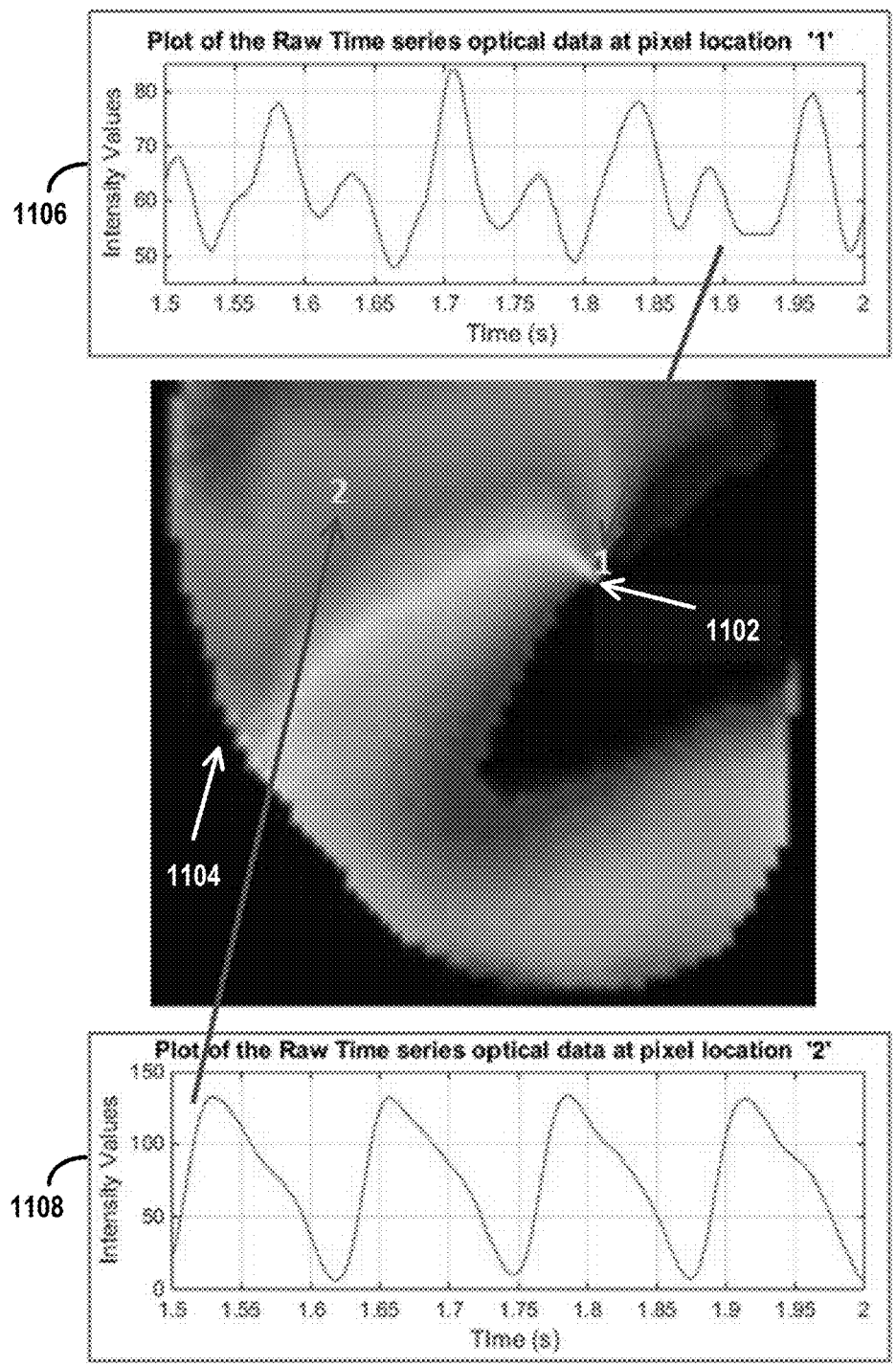
FIG. 11 illustrates an exemplary graphic identifying a rotor and its pivot point using a snapshot of a phase movie from an optical mapping animal experiment illustrated in FIG. 3. Additionally.

In instances using electrograms, each electrogram of the plurality of electrograms may correspond to a unique spatial location of the heart and each electrogram of the plurality of electrograms may include a plurality of intensity values (such as voltages) over a time series (such as shown partially by the amplitude plots of FIGS. 5 and 11). Whether using electrograms or optical mapping experiments, different locations of the heart can be represented by respective sets of data.

At 202a', a processor of the system may generate a histogram using the raw data 201. In an example, the processor may generate an output for displaying the histogram on a display device. Then at 202a", the processor can determine PDF according to the histogram and/or the raw data 201. In some examples, at 202a', the processor may generate histograms using the sets of data and a symbolic dynamics approach described herein. This last-mentioned operation or another type of histogram generation may include binning each electrogram of the plurality of electrograms (or each set of optical data) according to amplitude, which results in a plurality of bins per electrogram (or per set of optical data). Each bin of the plurality of bins represents an amplitude or amplitude range and includes a frequency of occurrences of the amplitude or amplitude range. In an example, these bins may be displayed as a histogram as well. Respectively, the operation at 202a" may also include determining a probability density of each bin of the plurality of bins, per electrogram (or per set of optical data).

Figure 13:
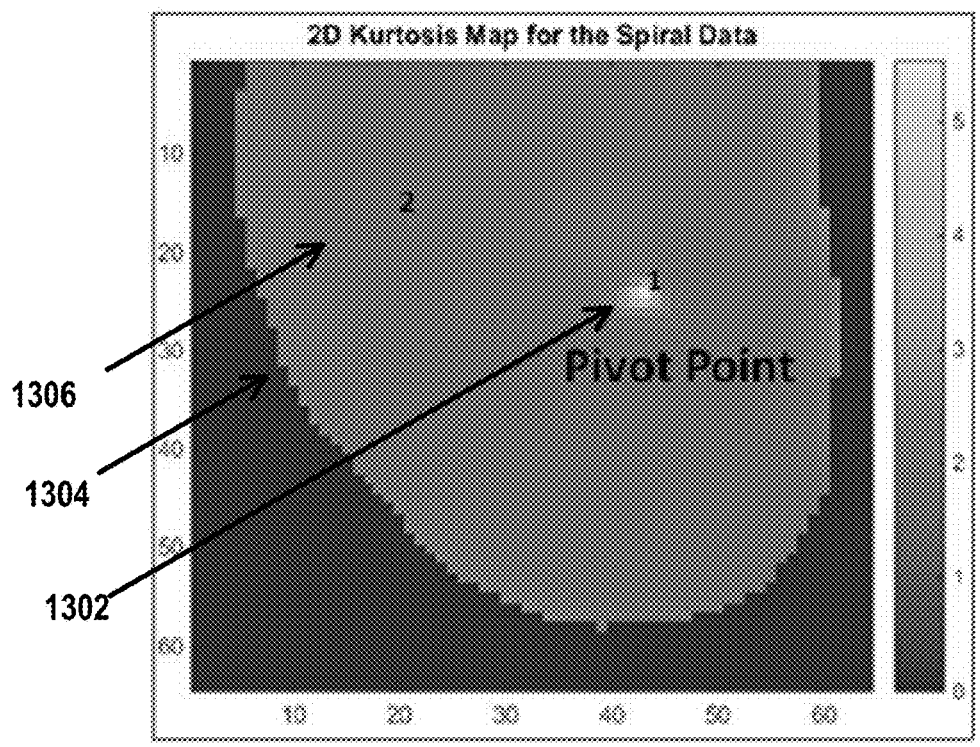
FIG. 13 illustrates an exemplary graphic identifying a rotor and its pivot point using a kurtosis map derived from optical mapping data corresponding to the rotor depicted in FIG. 3.

At 204a, a processor of the system may determine a kurtosis value using the kurtosis approach. In an example, with the determination of kurtosis values, the processor may generate a 2D kurtosis map (such as shown in FIG. 13). In generating the map, the processor may use the kurtosis approach to determine kurtosis values at multiple spatial locations of the heart. Then, the processor can map those values to their respective spatial locations of the heart in the map. Input for the kurtosis approach can include the histograms and/or the PDFs generated and determined respectively at operations 202a' and 202a". The histogram and/or PDFs can be generated and determined at each measured spatial location of the studied heart.

Figure 8:
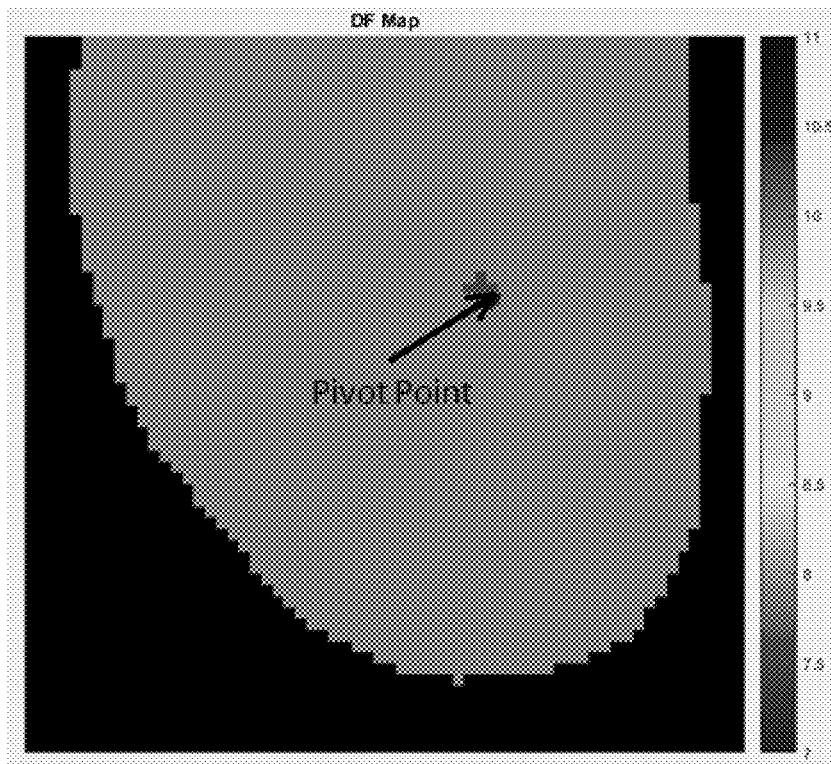
FIG. 8 illustrates an exemplary graphic identifying a rotor and its pivot point using a DF map derived from the snapshot of FIG. 3.

At 202b, a processor of the system may determine a dominant frequency (DF) using the raw data 101. In an example, with the determination of the DF, the processor may generate a 2D DF map (such as shown in FIG. 8) or 3D DF map using the raw data 201. At 204b, a processor of the system may determine a multi-scale frequency at each pixel of the map using the MSF approach described herein. In an example, with the determination of i-MSF per pixel, the processor may generate a 2D or 3D i-MSF map using the MSF approach. Input for the MSF approach can include 2D DF maps generated at operation 202b.

Figure 20:
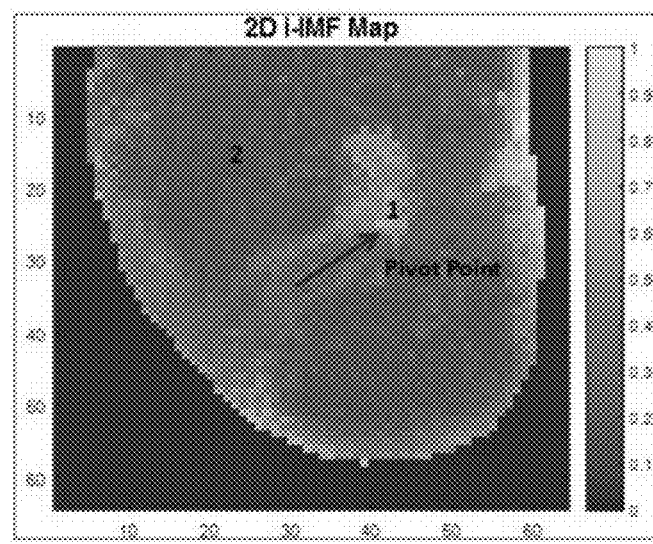

At 202c', a processor of the system may generate an i-IMF dataset using the EMD approach described herein and the raw data 101. At 202c", the processor, for each IMF value can compute a moving-averaged time series. In an example, with the further determination of the i-IMF dataset at 202c", the processor may generate a 2D i-IMF map (such as shown in FIG. 20) or 3D DF map using the raw data 201. At 204c, a processor of the system may determine i-IMF values of the dataset using an MSE approach described herein, such as for each pixel of the map. In an example, with the determination of i-IMF value per pixel, the processor may generate a 2D or 3D i-IMF map using the EMD and/or an MSE approach. Although not depicted in FIG. 2, input for these approaches can include 2D DF maps generated at operation 202b, or the histograms generated at 202a' for example.

Figure 25:
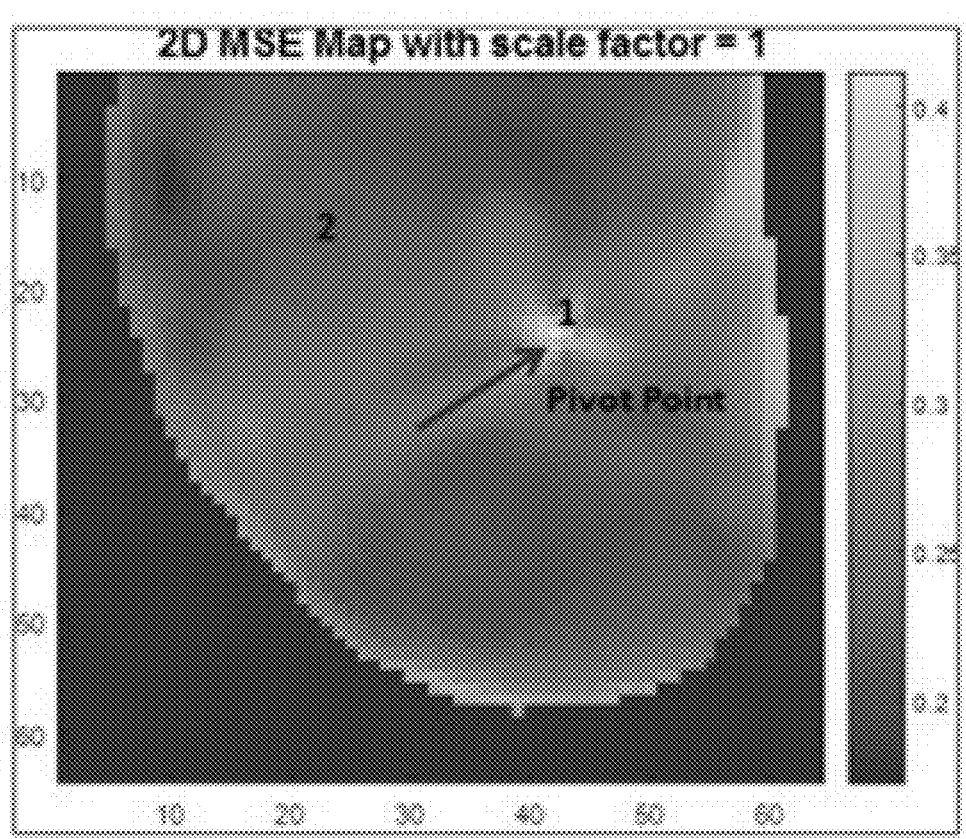
FIGS. 25-27 illustrate exemplary graphics identifying the rotor and its pivot point using different MSE maps with different scale factors, wherein each of these maps is derived from optical mapping data corresponding to the rotor depicted in FIG. 3.
Figure 26:
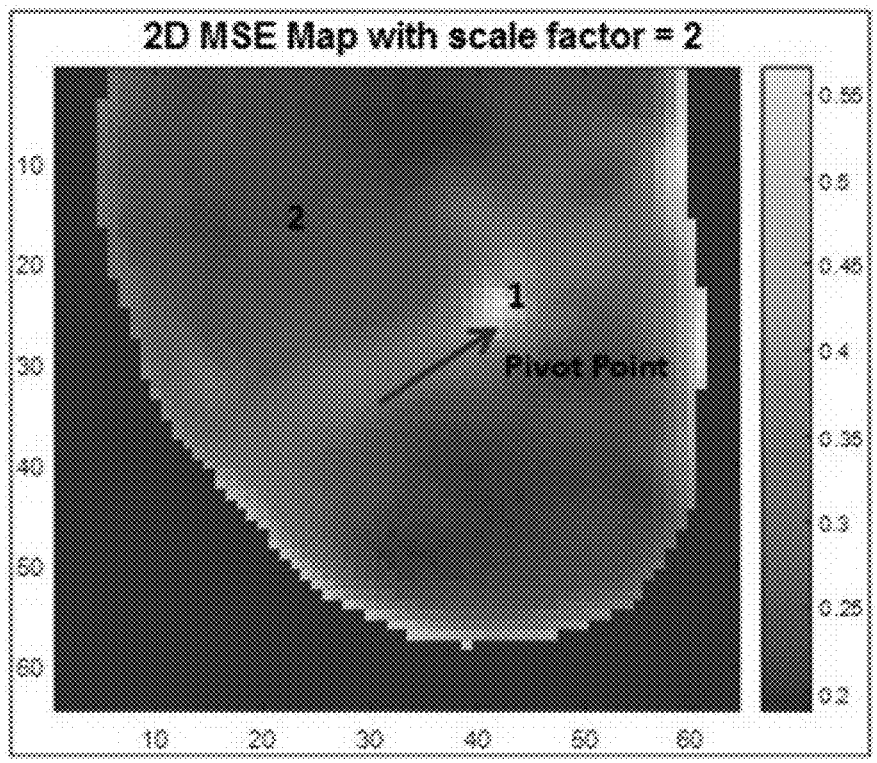
Figure 27:
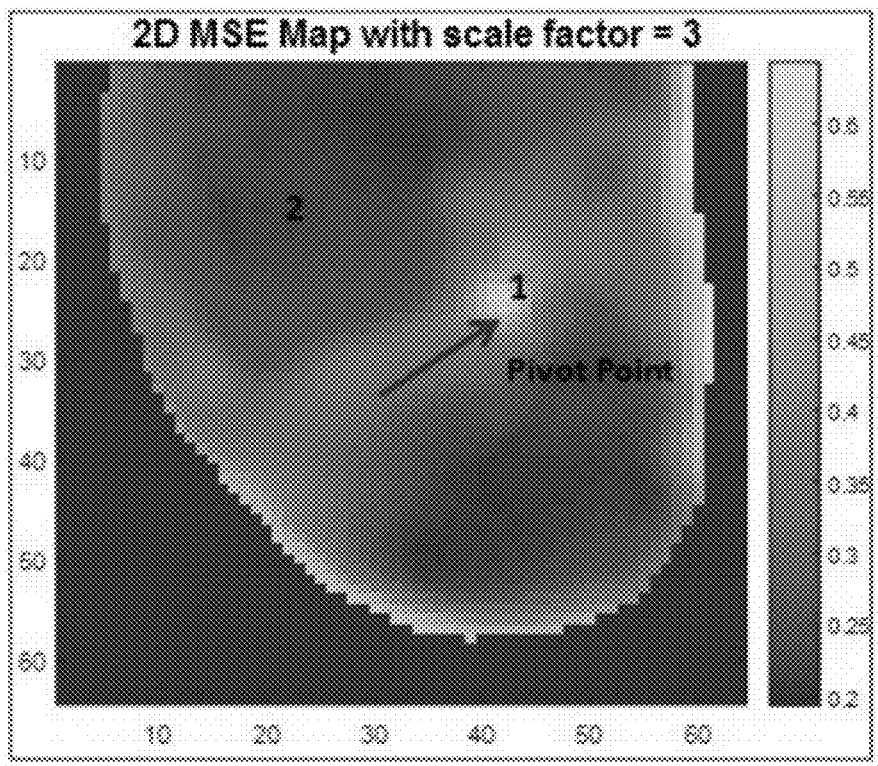

At 202d, a processor of the system may generate an MSE dataset using one of the MSE approaches described herein and the raw data 201. In an example, the processor may also generate one or more 2D or 3D MSE maps according the MSE approach, the raw data 201, and the scale factors used (such as illustrated by FIGS. 25-27). At 202d, the processor may determine MSE values of the dataset using the MSE approach, such as for each pixel of the map. In an example, with the determination of MSE value per pixel, the processor may generate a 2D or 3D MSE map. Although not depicted in FIG. 2, input for these approaches can include 2D DF maps generated at operation 202b, or the histograms generated at 202a' for example.

At 206, the processor may include outputting, for display on a display device, the 2D kurtosis map, the 2D i-MSF map, the 2D i-IMF map, the 2D MSE maps, variations thereof, or any combination thereof. One more of the maps can be displayed simultaneously such that they can be compared and the comparison can be used to more precisely locate an aspect of a rotor such as the pivot point. In some embodiments, the mapping can occur over a 2D or 3D image of the heart. Also, the amount of kurtosis, the i-MSF value, the i-IMF value, or the 2D MSE value at a particular location can correspond to a range of different colors, shades of a gray or another color, different symbols, or indexed values each of the range corresponding to a value such that displaying such graphical indicators shows kurtosis, MSF, EMD, or MSE levels at different locations in the heart depending on the mathematical approach used.

At 208, the processor automatically or a user of the system manually can identify an indicator part of a rotor in a fibrillation according to at least one of an analysis and/or map of operations 202a', 202a", 204a, 202b, 204b, 202c', 202c", 204c, 202d, and 206. In one example, where the processor automatically identifies a pivot point or some other indicator part of the rotor, an actual map may not be displayed and identification of the pivot point or the other indicator part may be solely according to the analysis and determinations of operations 202a', 202a", 204a, 202b, 204b, 202c', 202c", 204c, or 202d. In other words, in automated identification of a rotor part, displaying of the map can be excluded. Alternatively, or additionally, at 208, the processor can identify a pivot point or another type of indicator part according to one or more of the maps describe herein. For example, at 206, the processor can optionally communicate a map generated at operation 202a', 202a", 204a, 202b, 204b, 202c', 202c", 204c, or 202d to a display device communicatively coupled to the processor, and the display device can then display one or more of the maps. The maps may include a two-dimensional (2D) or a three-dimensional (3D) image of the mapped heart. Then, according to one or more of the maps, the processor automatically (or a user manually) can identify a pivot point or another type of indicator part of a rotor in a fibrillation, at 208.

Finally, at 210, a condition of the heart can then be treated according to at least the identified indicator part of the rotor. At 210, the processor output a signal to at least partially control a mechanism to treat a condition of the heart according to at least the identified indicator part of the rotor, or a user of the system, such as a surgeon, can manually treat a condition of the heart according to at least the identified indicator part of the rotor. In an embodiment, the treating of the condition of the heart can include ablating the heart according to at least the identified indicator part of the rotor. For example, a catheter-based ablation procedure that is customized for the patient can be designed according to at least the identified indicator part of the rotor.

An Exemplary Device that can Implement the Operations Disclosed Herein

Figure 4:
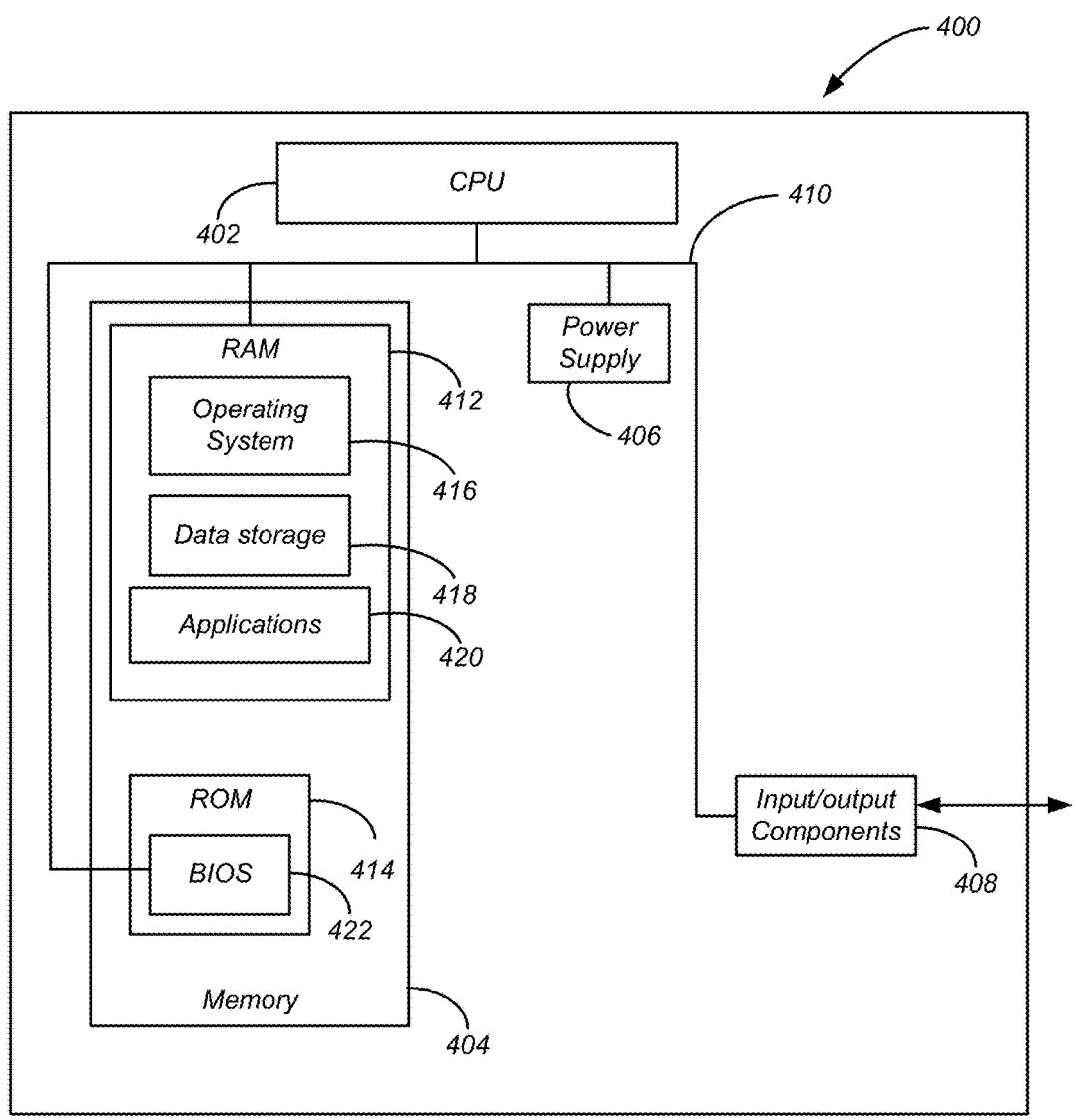
FIG. 4 illustrates a block diagram of an exemplary device that can implement at least some of the operations illustrated in FIGS. 1, 2, 7, 10, 16, and 23.

FIG. 4 illustrates a block diagram of an exemplary electronic device 400 that can implement aspects of methods disclosed herein that can provide operations, such as one or more of the operations described herein including those illustrated in FIGS. 1, 2, 7, 10, 16, and 23. The electronic device 400 can include a central processing unit (CPU) 402, memory 404, a power supply 406, and input/output components 408, and a communication bus 410 that connects the aforementioned elements of the electronic device. The CPU 402 can be any type of data processing device or processor, such as a CPU. Also, the CPU 402 can include one or more data processing devices or processors that may be in combination with local or remote memory. Also, for example, the CPU 402 can be central processing logic. The memory 404, which can include random access memory (RAM) 412 or read-only memory (ROM) 414, can be enabled by one or more memory devices. The one or more memory devices may also be local or remote with respect to the electronic device 400 or the CPU 402. The RAM 412 can store data and instructions defining an operating system 416, data storage 418, and applications 420, such as applications implemented through hardware including circuitry that can implement the operations illustrated in FIGS. 1, 2, 7, 10, 16, and 23. The applications 420 may include hardware (such as circuitry and/or microprocessors), firmware, software, or any combination thereof. The ROM 414 can include basic input/output system (BIOS) 422 of the electronic device 400. The memory 404 may include a non-transitory medium executable by the CPU. For example, the memory 404 can include a non-transitory medium with instructions executable by a processor to cause the processor (such as the CPU)

to perform any of the operations disclosed herein, such as the operations described with respect to FIGS. 1, 2, 7, 10, 16, and 23.

The power supply 406 contains power components, and facilitates supply and management of power to the electronic device 400. The input/output components 408 can include circuitry for facilitating communication between any components of the electronic device 400, components of external devices, and end users. The I/O components 408 can include user interfaces such as monitors, keyboards, touchscreens, microphones, and speakers. Further, some of the I/O components 524 can facilitate communication between components of the electronic device 400, and can ease processing performed by the CPU 402. The bus 410 may provide such functionality as well.

The electronic device 400 can send and receive signals, such as via a wired or wireless network, or may be capable of processing or storing signals, such as in memory as physical memory states. The device 400 can include or be communicatively coupled to a server, dedicated rack-mounted servers, a personal computer, and/or an integrated device combining various features disclosed herein such as laboratory hardware or a medical device including an integrated computing device.

The MSF Approach

Figure 7:
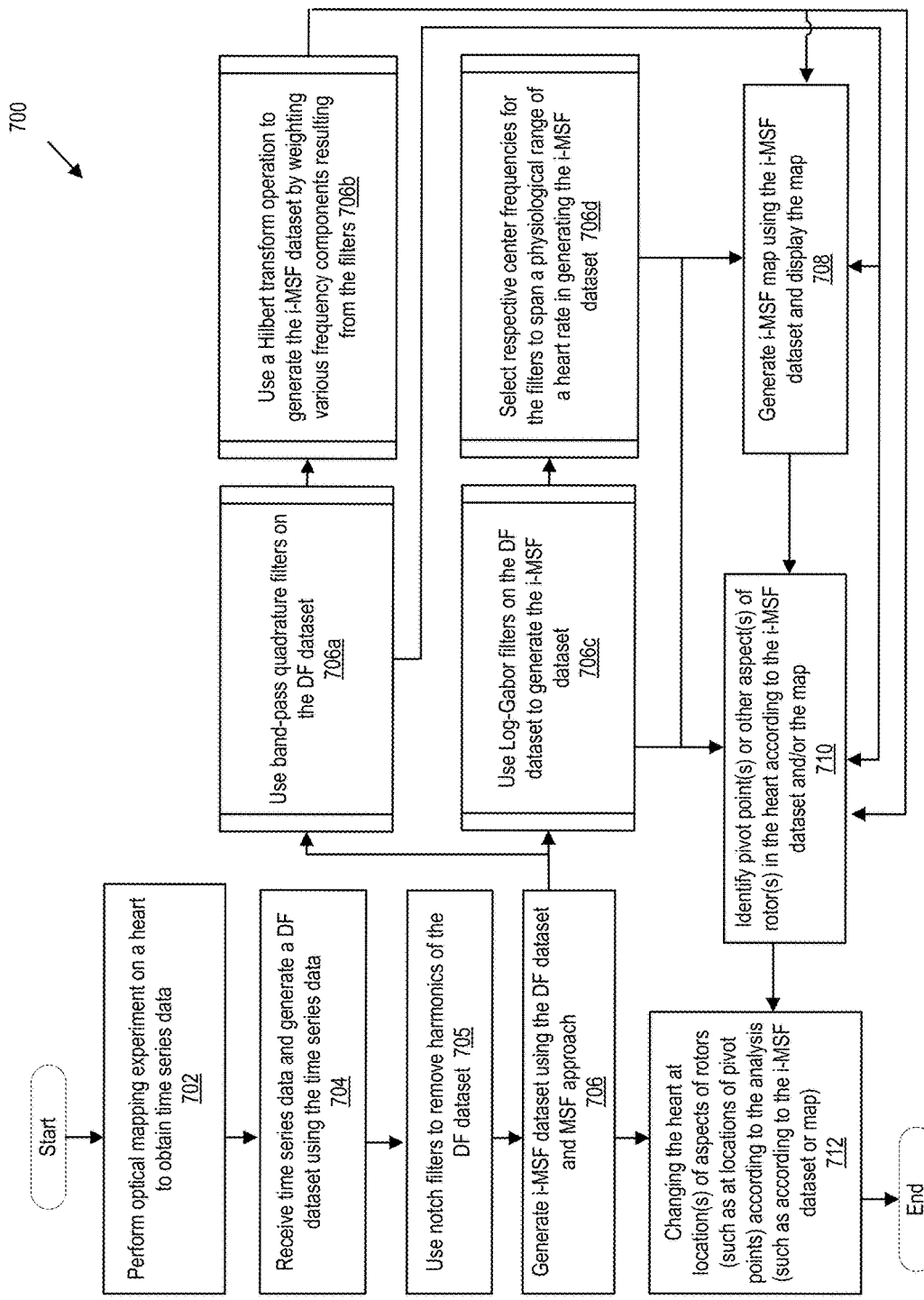
FIG. 7 illustrates exemplary operations performed by a system that can implement rotor identification in a fibrillation, such as an atrial fibrillation, using MSF calculations.

FIG. 7 illustrates exemplary operations 700 performed by a system that can implement rotor identification in a fibrillation, such as atrial or ventricular fibrillation, and treat the fibrillation accordingly. Operations 700 form a method for identifying and treating a pivot point or some other aspect of a rotor in a fibrillation (such as an atrial or ventricular fibrillation). The operations 700 include performing an optical mapping experiment feasible on human or animal hearts, including any in vivo or in vitro experiment to obtain time series data, at 702. As mentioned, FIG. 3 illustrates an example of a single rotor in an isolated rabbit heart from optical mapping experiments. In FIG. 3, the pivot point of the rotor is indicated by an arrow. FIG. 3 is an exemplary snapshot of a phase movie, where different colors represent different phases of action potential. The convergence of different phases may correspond to a singularity point, e.g., the pivotal point or core of the rotor, which can be identified by the arrow.

The operations 700 include receiving, by a processor (such as CPU 402 illustrated in FIG. 4), at 704, the time series data obtained from a plurality of electrograms or electrical potential readings of a heart. As mentioned herein, the electrograms can be derived from electrical potential readings, such as those described herein. In instances using electrograms, each electrogram of the plurality of electrograms corresponds to a different spatial location (such as a different unique spatial location) in the heart and each electrogram of the plurality of electrograms includes a plurality of electrical potential readings over a time series. These readings may be voltage readings (such as shown by chart 502*a* of FIG. 5). Also, different locations in the heart are represented by respective sets of data.

Additionally, at 704 (not depicted), the processor may generate histograms using the sets of data and the symbolic dynamics approach disclosed herein. The symbolic dynamics approach may include binning each electrogram of the plurality of electrograms (such as binning each set of electrical potentials) according to amplitude, which results in a plurality of bins per electrogram. Each bin of the plurality of bins represents an amplitude or amplitude range of the electrical potentials and includes a frequency of occurrences of the amplitude or amplitude range. The bins may be displayed as a histogram, such as shown by histogram 502*b* of FIG. 5. The operation at 704 may also include determining a probability density of each bin of the plurality of bins, per electrogram (not depicted). The histogram may also be displayed after the determination of the probability densities.

Also, at 704, a processor of the system determines a DF using the time series data. Further, the DF may be determined using the probability densities from the symbolic dynamics approach. In an example, with the determination of the DF, the processor may generate a two-dimensional (2D) DF map (such as shown in FIG. 8). For example, the processor may use the time series data or the probability densities. Operation 704 may also include displaying the 2D DF map. In some examples, a three-dimensional (3D) image of the heart may be generated and/or displayed as well.

Figure 9:
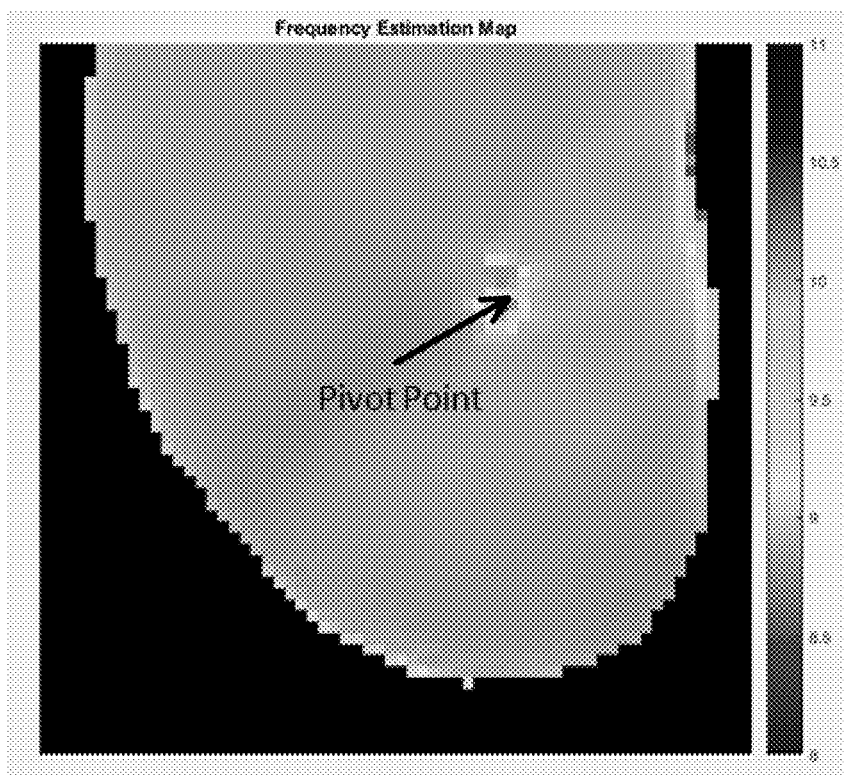
FIG. 9 illustrates an exemplary graphic identifying a rotor and its pivot point using a multi-scale frequency index (i-MSF) map derived from the snapshot of FIG. 3 and/or data associated with the graphic of FIG. 8.

At 706, the processor may determine an i-MSF using the MSF approach. In an example, with the determination of i-MSF, the processor may generate a 2D i-MSF map (such as shown in FIG. 9) using the MSF approach. Input for the MSF approach can include 2D DF maps generated at operation 104. The MSF approach is described in this section in more detail herein, with reference to operations 706, 706*a*-706*d*, and 708.

At 710, in an example, the processor can identify a pivot point or another indicator part of a rotor in a fibrillation according to the analysis and determinations of operations 704-708. For example, where the processor automatically identifies a pivot point or some other indicator part of the rotor, an actual map may not be displayed and identification of the pivot point or the other indicator part may be solely according to the analysis and determinations of operations 704-706 and 706*a*-706*d*. In other words, in automated identification of a rotor part, displaying of the map at 708 can be excluded. Alternatively, or additionally, at 710, the processor can identify a pivot point or another type of indicator part according to one or more of the maps describe herein. For example, at 106, the processor can optionally communicate any one of the maps described herein to a display device communicatively coupled to the processor, and the display device can then display one or more of the maps. Then, according to one or more of the maps, the processor automatically (or a user manually) can identify a pivot point or another type of indicator part of a rotor in a fibrillation, such as at 710.

At 712, a condition of the heart can then be treated according to at least the identified indicator part of the rotor. In an exemplary embodiment, the treating of the condition of the heart can include ablating the heart according to at least the identified indicator part of the rotor. For example, a catheter-based ablation procedure that is customized for the patient can be designed according to at least the identified indicator part of the rotor.

Referring back to the MSF approach, as mentioned, at operation 706, the processor may generate an i-MSF map (such as shown in FIG. 9) using the MSF approach. The MSF approach can include use band-pass quadrature filters on the DF dataset at 706*a*. Band-pass quadrature filters can estimate local multi-scale information, such as the energy, phase, radial frequency and orientation/angular frequency of specific location of a heart. The MSF approach can also use a Hilbert transform operation to transform a real-valued signal to an analytic signal with no negative frequencies at 706*b*. When combined with the band-pass quadrature filters, the Hilbert transform can generate MSF information by weighting various frequency components resulting from the filters. The resulting datasets from operations 706a and 706b can then be used to generate and display the map at 708 and/or identify aspects of the rotor at 710.

In the depicted example of FIG. 7, Log-Gabor filters can be used (such as eight Log-Gabor filters can be used with a relative filter bandwidth B of 2√2, each being one octave apart). Such filters can be used on the DF dataset at 706c. In some exemplary embodiments, such as shown in FIG. 7, the respective center frequencies for the Log-Gabor filters can be selected to span a physiological range for a heart rate at 706d. The resulting datasets from operations 706c and 706d can then be used to generate and display the map at 708 and/or identify aspects of the rotor at 710.

In addition, the signal can be filtered using notch filters to remove harmonics of the DF map, such as at operation 705.

In some exemplary embodiments, a wide-range local MSF value i-MSF, can be obtained by a weighted summation over the eight different filter pairs using Equation (1) of this section. In Equation (1) of this section, $q_i$ is the output of the ith Log-Gabor filter and $\rho_0$ is the center frequency of the first Log-Gabor filter. In an example, the i-MSF is expected to be different at the rotor pivot point compared to the periphery which can enable the pivot point's identification.

$$i\text{-MSF} = \rho_o [\Sigma_{i=1}^{N-1} q_i]^{-1} \Sigma_{i=1}^{N-1} 2^{i+0.5} q_{i+1} \quad (1)$$

Log-Gabor filters are used because they are known to better encode natural images compared with the original Gabor filter and in some instances a Fourier Transform filter. A one-dimensional Log-Gabor function has the frequency response provide by Equation (2) of this section.

$$G(f) = \exp\left(\frac{-(\log(f/f_0))^2}{2(\log(\sigma/f_0))^2}\right) \quad (2)$$

In Equation 2 of this section, $f_0$ and $\sigma$ are the parameters of the filter. $f_0$ will give the center frequency of the filter. $\sigma$ affects the bandwidth of the filter. It is useful to maintain the same shape while the frequency parameter is varied. To do this, the ratio $\sigma/f_0$ can be configured to remain constant.

Alternatively, Log-Gabor filters can be used as a probability distribution function, with a normal distribution. In such an example, the logarithm of the frequencies is also used, and the one-dimensional Log-Gabor function has the modified frequency response provided by Equation 3 of this section.

$$G(f) = \frac{f_0}{f} \exp\left(\frac{-(\log(f/f_0))^2}{2(\log(\sigma/f_0))^2}\right) \quad (3)$$

In both of the aforementioned definitions of Log-Gabor filters, because of a zero value at a DC value, it is not possible to derive an analytic expression for the filter in the space domain. Thus, in some examples of mapping, the filters are configured in the frequency domain, and then an inverse Fourier transform generates the time domain impulse response.

Also, a two-dimensional extension of the Log-Gabor filter can be used. In 2D, the filter can be configured to a particular frequency and a particular orientation. The orientation component may be a Gaussian distance function according to the angle in polar coordinates, as shown by Equation 4 of this section.

$$G(f, \theta) = \exp\left(-\frac{(\log(f/f_0))^2}{2(\log(\sigma_f/f_0))^2}\right) \exp\left(\frac{-(\theta-\theta_0)^2}{2\sigma_\theta^2}\right) \quad (4)$$

In 2D, there are four parameters: $f_0$ the center frequency, $\sigma_f$ the width parameter for the frequency, $\theta_0$ the center orientation, and $\sigma_\theta$ the width parameter of the orientation. An example of this filter is shown by Equations 5 and 6 of this section.

The bandwidth in the frequency is given by:

$$B = 2\sqrt{2/\log(2)}(\|\log(\sigma_f/f_0)\|) \quad (5)$$

The angular bandwidth is given by:

$$B_\theta = 2\sigma_\theta\sqrt{2\log 2} \quad (6)$$

In some exemplary applications, a set of such filters are included in a filter bank. The filter bank may be designed using the minimum and maximum frequencies, the filter bandwidth, the number of orientations, the angular bandwidth, the filter scaling and the number of scales.

As mentioned herein, FIG. 8 illustrates an exemplary 2D DF map showing uniform DF throughout the rotor zone identified in FIG. 3. The pivot point is indicated by the arrow in FIG. 3. FIG. 8 shows the 2D DF map with uniform DF throughout the rotor zone as expected, for this experiment, at 7.9 Hz.

FIG. 9 illustrates an exemplary i-MSF map showing the identification of the pivot point. FIG. 9 shows the i-MSF map that identifies the rotor pivot point with a higher i-MSF of approximately 11 Hz compared to the periphery region as indicated by the arrow. FIG. 9 shows an exemplary 2D i-MSF map calculated for the same rotor illustrated in at least FIGS. 3 and 8. Note that an i-MSF map can provide for direct identification of the pivot point (see the arrow). Also, note that the i-MSF values are higher at the pivot point, and surrounding a spiral of higher values is a surrounding region of low i-MSF values. The spiral with higher values can provide for identification of the pivot point.

In an example of the experiments, the mapping data with a single rotor having a single DF of 7.9 Hz uniform throughout the DF map was expected. However, this DF value alone is limited for identification of the rotor pivot point. The chaotic nature at the rotor pivot point yields more frequency components other than the DF. These various frequency components can be processed through the various aforementioned filters, such as the filter described by Equation (1) of this section or any one of the Log-Gabor filters described herein. The results of filtering can include a frequency index different than DF which more accurately can identify the rotor pivot point. For example, the results are depicted in the i-MSF map shown in FIG. 9. As predicted, in the experiment, the periphery of the rotor was more uniform with the DF due to the less chaotic nature in this region compared to the pivot point and was slightly higher than DF at 9 Hz.

The MSF approach demonstrates the feasibility to accurately identify the rotor pivot point taking into account the combined mechanistic and electrical properties of the rotor with various frequency components that are different than the periphery. Exemplary studies with multiple rotors can demonstrate the efficacy of this approach in accurately identifying the pivot point of the rotors based on the MSF index. This also provides that that an application of the MSF approach to raw intra-atrial electrograms from persistent AF patients can be useful to identify active substrates that cause and maintain AF outside the PV region.

The Kurtosis Approach

Figure 10:
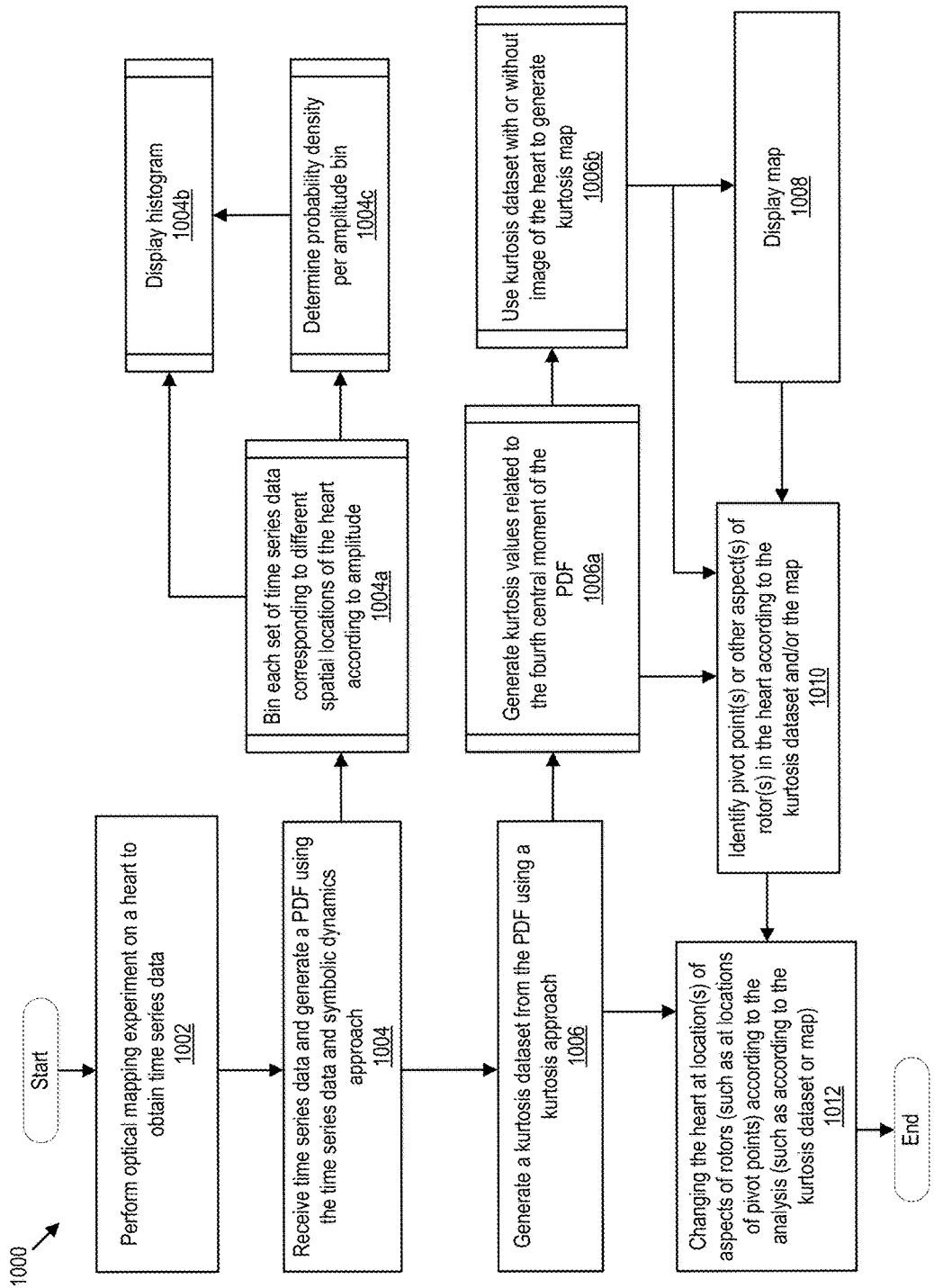
FIG. 10 illustrates exemplary operations performed by a system that can implement rotor identification in a fibrillation, such as an atrial fibrillation, using kurtosis calculations.

FIG. 10 illustrates exemplary operations 1000 performed by a system that can implement rotor identification in a fibrillation, such as atrial or ventricular fibrillation, and treat the fibrillation accordingly. Operations 1000 form a method for identifying and treating a pivot point or some other aspect of a rotor in a fibrillation (such as an atrial or ventricular fibrillation). The operations 1000 include performing an optical mapping experiment feasible on human or animal hearts, including any in vivo or in vitro experiment to obtain time series data, at 1002. As mentioned, FIG. 3 (as well as FIG. 11) illustrates an example of a single rotor in an isolated rabbit heart from optical mapping experiments. In FIGS. 3 and 11, the pivot point of the rotor is indicated by an arrow and a label "1". FIGS. 3 and 11 are exemplary snapshots of a phase movie, where different colors represent different phases of action potential. The convergence of different phases may correspond to a singularity point, e.g., the pivotal point or core of the rotor, which can be identified by the arrow and label "1".

The operations 1000 include receiving, by a processor (such as CPU 402 illustrated in FIG. 4), at 1004, the time series data obtained from a plurality of electrograms or electrical potential readings of a heart, and generating a PDF using the time series data and the symbolic dynamics approach. As mentioned herein, the electrograms can be derived from electrical potential readings, such as those described herein. In instances using electrograms, each electrogram of the plurality of electrograms corresponds to a different spatial location (such as a different unique spatial location) in the heart and each electrogram of the plurality of electrograms includes a plurality of electrical potential readings over a time series. These readings may be voltage readings (such as shown by chart 502a of FIG. 5 and by charts 1106 and 1108 of FIG. 11). Also, different locations in the heart are represented by respective sets of data.

Additionally, at 1004, the processor may generate histograms using the sets of data and the symbolic dynamics approach disclosed herein. The symbolic dynamics approach may include binning each electrogram of the plurality of electrograms (such as binning each set of electrical potentials) according to amplitude at 1004a, which results in a plurality of bins per electrogram. Each bin of the plurality of bins represents an amplitude or amplitude range of the electrical potentials and includes a frequency of occurrences of the amplitude or amplitude range. At 1004b, the bins may be displayed as a histogram, such as shown by histogram 502b of FIG. 5. The operation at 1004 may also include determining a probability density of each bin of the plurality of bins, per electrogram, at 1004c. The histogram may also be displayed after the determination of the probability densities.

At 1006, a processor of the system may determine a kurtosis value using the kurtosis approach and the PDF generated at 1004. In an example, with the determination of kurtosis values, the processor may generate a 2D kurtosis map (such as shown in FIG. 13). In generating the map, the processor may use the kurtosis approach to determine kurtosis values at multiple spatial locations of the heart. Then, the processor can map those values to their respective spatial locations of the heart in the map. Input for the kurtosis approach can include the histograms and/or the PDFs generated and determined respectively at operations 1004a-1004c. The histogram and/or PDFs can be generated and determined at each measured spatial location of the studied heart. The kurtosis approach is described in more detail in this section below.

Operation 1006 may also include generating a kurtosis dataset from the PDF using the kurtosis approach and/or generating an kurtosis map by mapping the kurtosis values and/or dataset to their corresponding spatial locations in the heart at 1006b. Such mapping can occur over a 2D or 3D image of the heart, for example. Also, the amount of kurtosis per location can correspond to a color of a range colors, shades, symbols, or values such that the kurtosis map, through the use of such elements, shows kurtosis levels at different locations in the heart (such as shown by FIG. 13).

Alternatively, or in addition to generating a map, the system can display graphical indicators of the plurality of kurtosis values corresponding to the plurality of spatial locations in the heart using a display device at 1008. The graphical indicators of the plurality of kurtosis values can include a range of different colors, shades of a gray or another color, different symbols, or indexed values. Each of such visual elements of the range can correspond to a kurtosis value such that the displaying of the graphical indicators of the plurality of kurtosis values shows kurtosis levels at different locations in the heart.

At 1008, the kurtosis map is displayed on a display device, such as the monitor or display device (see for example input/output components 408 of FIG. 4 which may include a display device). According to the kurtosis dataset and/or map, the processor automatically (or a user manually) can identify a pivot point or some other aspect of a rotor in a fibrillation at 1010. In an example where the processor automatically identifies a pivot point or some other aspect of the rotor, the actual map may not be displayed. In other words, in automated identification of a rotor part displaying of the map is not necessary.

Finally, at 1012, the system can physically change the heart at one or more of the locations of the aspects of the rotors (such as at the locations of pivot points) according to the analysis such as according to the kurtosis dataset or map. In exemplary embodiments, the changing of the heart can include catheter ablations at the locations of the pivot points of the rotors in the heart.

Referring back to operation 1006b of operation 1006, a processor of the system may generate a kurtosis map (such as shown in FIG. 13) using a kurtosis approach. The kurtosis approach can include using a higher order statistics approach by estimating kurtosis values of the electrogram data for multiple spatial locations of the studied heart. Such higher order statistics can be useful since the electrogram data can include non-Gaussian or nonlinear processes. Kurtosis or the fourth central moment includes a measurement of the peakedness of a PDF of a random variable, such as a real-value corresponding to the peakedness. Thus, the operations 1000 can include generating kurtosis values related to the fourth central moment of the PDF at 1006a. A higher kurtosis value (e.g., kurtosis>3) can mean that more variances are present in electrocardiogram (ECG) data due to infrequent extreme deviations. Such a level of kurtosis can show a pivot zone of rotor. In other words, it has been discovered that a characteristic of a pivot zone of a rotor can be that its kurtosis will be higher than the kurtosis at the periphery of the rotor. At the periphery of the rotor, more frequent modestly sized deviations occur in ECG data and lower kurtosis values are usually shown (e.g., kurtosis<3)

As mentioned, the kurtosis approach described herein can be applied to the time series data, such as optical fluorescence recordings, obtained during imaging of electrical activity of a heart. For example, the kurtosis approach can be applied to optical fluorescence recordings of an isolated rabbit heart for experimentation, as well as intra-atrial electrograms obtained from patients. Then, in an exemplary embodiment, a processor of the system can obtain a PDF by creating amplitude bins and a histogram of the optical fluorescence data or the intra-atrial electrogram data.

FIG. 11 shows an exemplary graphical representation of a single rotor obtained from optical mapping experiments of an isolated rabbit heart. In FIG. 11, the pixel labeled '1' represents the approximate region of a rotor pivot point and the pixel labeled '2' corresponds to a region in the periphery of the rotor. Also depicted is an estimated location 1102 of the pivot point of the rotor 1104. Also, as illustrated in the top plot of FIG. 11, the changing wave front direction near the pivot point can cause a broader distribution in the optical mapping data. The top plot 1106 also shows more peakedness than the peakedness in the bottom plot 1108, which can be measured by kurtosis. In other words, the bottom plot 1108 (which is representative of the periphery region of the rotor) is more uniform and thus less peakedness than the top plot 1106. Given the result of the bottom plot 1108, it should have a lower kurtosis. Hence, kurtosis mapping technique can enable accurate identification of a rotor pivot point and rotor periphery. Thus, such mapping techniques can be used to generate patient specific kurtosis maps to guide AF ablation, for example.

A kurtosis value or a value related to the forth central moment can be determined at 1006a such as according to Equation (1) of this section that is shown below.

$$Kurt(X) = E\left\{\left[\frac{X - E\{X\}}{\sigma}\right]^4\right\} = \frac{\mu_X^4}{\sigma_X^4} \quad (1)$$

The X in Equation (1) of this section is a stochastic univariate variable that describes a random process. The expectation E value or mean of a stochastic variable X is defined in Equation (2) of this section, which is shown below.

$$E\{X\} = \int_{-\infty}^{\infty} x \cdot f(x)dx = \mu_X \quad (2)$$

The x in Equation (2) of this section represents the time series data and f represents the PDF. The standard deviation $\sigma_X$ provided in Equation (1) of this section is given by Equation (3) of this section, as shown below.

$$\sigma_X = \sqrt{Var(X)} \quad (3)$$

The variance Var(X) that is related to the standard deviation, which can also be called the second central moment, is a measure of the spread of data. The variance can be given by Equation (4) of this section, as shown below.

$$Var(X) = E\{[X - E\{X\}]^2\} = \sigma_x^2 \quad (4)$$

Depending on the kurtosis value the signal can be classified as sub-Gaussian (e.g., kurtosis<3), super-Gaussian (e.g., kurtosis>3) and Gaussian (e.g., kurtosis=3).

Figure 12:
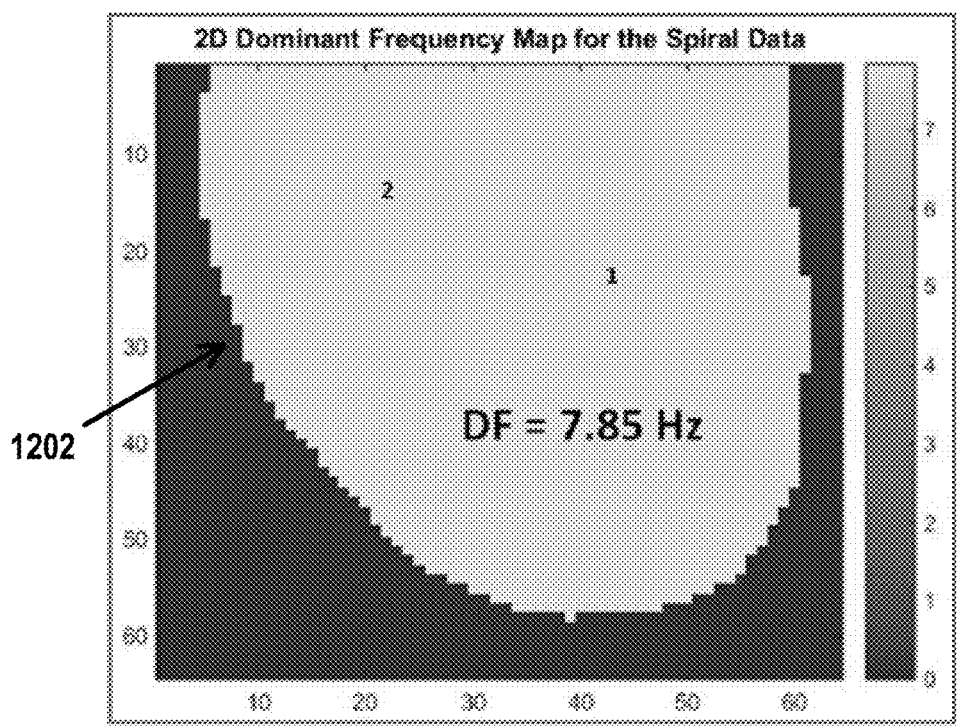
FIG. 12 illustrates an exemplary graphic of a DF map derived from optical mapping data corresponding to the rotor depicted in FIG. 3.

In an exemplary embodiment, a processor of the system can obtain phase movies from optical mapping such as the aforementioned kurtosis mapping. The processor can process the phase movies using 60 Hz notch filter to remove the 60 Hz noise. In such an example, the filtered optical data can be used to compute the kurtosis value using Equation (1) of this section. The processor can also generate a 2D kurtosis map using the kurtosis value at each pixel location across all the frames. Also, for comparison purposes, the processor can also generate a 2D DF map by taking temporal Fourier Transform of the optical mapping data from every pixel. In an example, the signal processing described herein can be implement via MATLAB. FIG. 12 depicts a 2D DF map based on such optical mapping data. FIG. 13 depicts a 2D kurtosis map based on such optical mapping data. Note that analogous maps can be generated similarly according to the other mathematical approaches described herein.

Referring back to FIG. 11, the depicted graphic shows a graphical representation of rotor 1104 in an isolated rabbit heart from optical mapping experiments. Pixel points labeled "1" and "2" represent regions near the pivot point and periphery, respectively, and the arrows point to the corresponding amplitude plots 1106 and 1108. The depicted rotor 1104 of an isolated rabbit heart shown in the graphic illustrated in FIG. 11 is a snapshot of a phase movie. The different colors in the graphic represent different phases of action potential. Note that the estimated location of the pivot point 1102 or core of the rotor can be easily identified as the point where different phases or colors converge. Note that the pixels near the estimated location of the pivot point 1102 are white or may be considered the lightest shade of grey depicted. This appears to be the case since all the representative colors of the phases of action potential are converging. Also, as depicted, the estimated pivot point is identified by a arrow and is at the pixel point labeled "1".

Referring to FIG. 12, the depicted map shows a 2D DF map showing uniform DF of 7.85 Hz throughout the rotor region 1202, which is displayed in grey. This demonstrates the inability of such a map to assist in identifying a rotor pivot point.

Figure 14:
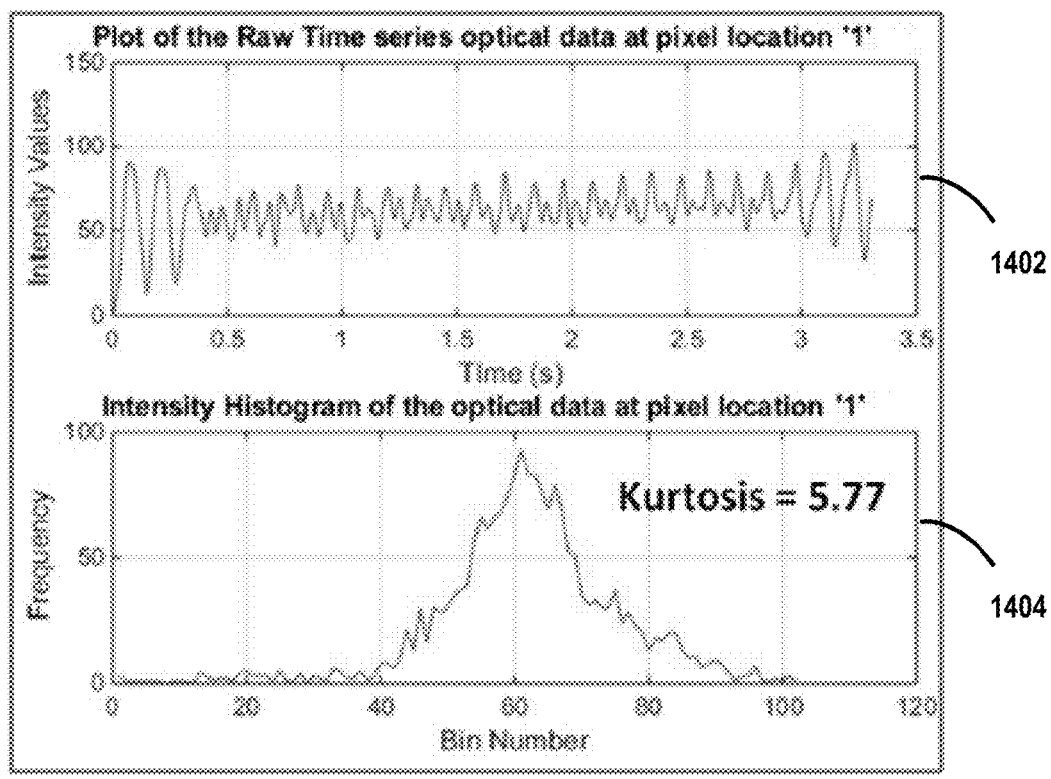
FIG. 14 illustrates an exemplary amplitude plot depicting optical data at a pixel location approximately at the pivot point of the rotor depicted in FIG. 13. Additionally.
Figure 15:
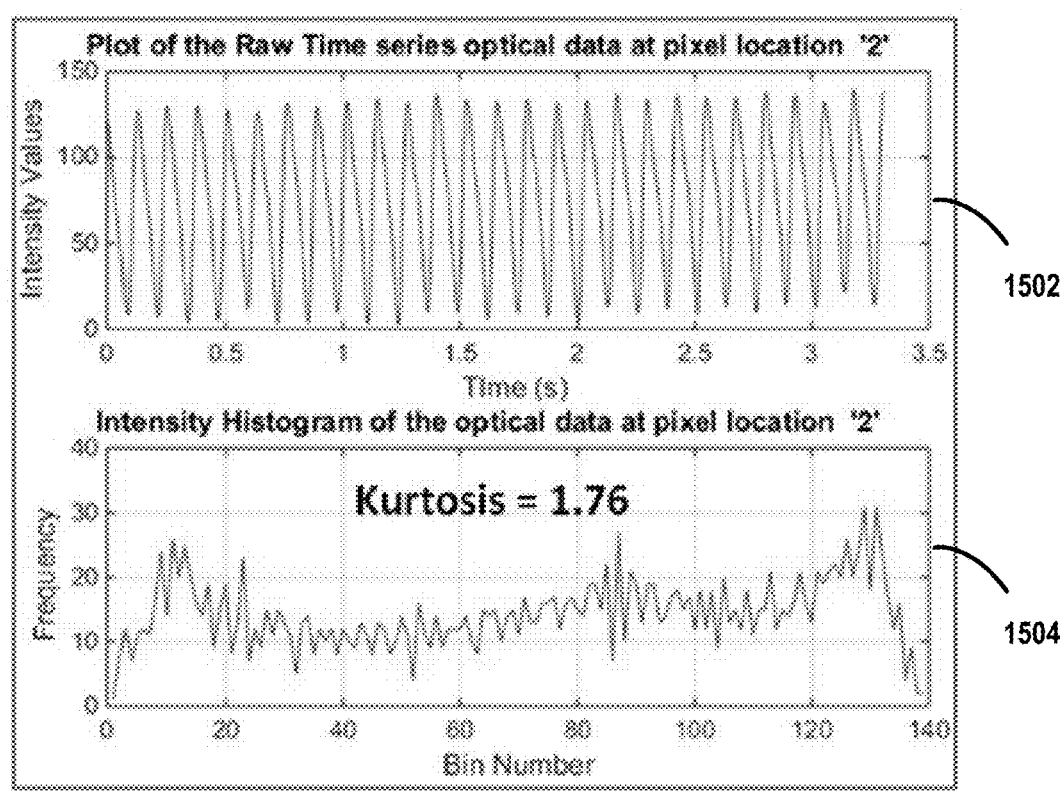
FIG. 15 illustrates an exemplary amplitude plot depicting optical data at a pixel location in the periphery of the rotor depicted in FIG. 13. Additionally.

FIG. 13 shows a 2D kurtosis map showing an identification of the rotor pivot point indicated by the arrow. The 2D kurtosis map is generated from the same optical data of the rotor depicted in FIG. 11. Because of the determined kurtosis values, which have been mapped in FIG. 13, the estimated pivot point of the rotor is clearly seen as a region with higher kurtosis values displayed as lighter shades of gray in comparison to the periphery of the rotor. The point with the highest presented kurtosis is displayed in the lightest shades of grey, and is estimated to be the pivot point 1302 of the depicted rotor 1304. As shown, the higher kurtosis values are represented by the lightest shades of grey depicted. The lower kurtosis values (such as kurtosis<3) are shown to be darker shades of grey and depict the periphery 1306 of the rotor 1304. With respect to FIG. 13, FIG. 14 depicts a plot 1402 of raw optical data at the pixel location labeled "1" near the estimated pivot point 1302 of the depicted rotor 1304. FIG. 14 also depicts an intensity histogram 1404 of the corresponding time series data, which reveals a kurtosis value of 5.77. Also, with respect to FIG. 13, FIG. 15 depicts a plot 1502 of raw optical data at the pixel location labeled "2", which is in the periphery 1306 of the depicted rotor 1304. FIG. 15 also depicts an intensity histogram 1504 of the corresponding time series data, which reveals a kurtosis value of 1.76. Note that analogous maps, plots, and histograms can be generated similarly according to the other mathematical approaches described herein.

In generating the graphic of FIG. 13, higher order statistics using the kurtosis approach was employed to accurately identify the estimated rotor pivot point 1302. As shown in FIGS. 14 and 15, the morphology of the optical mapping data changes significantly at the rotor pivot point compared to the periphery. This is reflected in the histograms of FIGS. 14 and 15. Also, the histograms show the "peakedness" that captures the chaotic nature of the electrograms at the pivot point 1302. The results indicate that kurtosis mapping could offer highly reliable and easy to compute patient-specific mapping of active rotor sites and pivot points.

The results of a study using the kurtosis approach, as shown in FIGS. 5 and 6, indicate accurate identification of rotor pivot point which provides promise for further validation of using the intra-atrial electrograms from a patient to visualize AF active substrates, especially at the rotor pivot point. Further, in some embodiments, a 3D kurtosis map can be generated that can provide real-time guidance to a physician or electrophysiologist performing ablation surgery in a patient specific manner. Further, the kurtosis approach may be used to identify rotor pivot points in paroxysmal and persistent AF patient data. Also, the kurtosis approach may be used to identify rotor pivot points that may cause and maintain AF in such patients. The other mathematical approaches described herein also provide such benefits.

Referring back to the operations at 1104, symbols can be created by amplitude bins and the information content of these symbols can be captured by kurtosis. Kurtosis is also a statistical measure of information content that can be based on the distribution of amplitude values within the signal histogram for example.

The spatial uncertainty of wave front direction in a part of a rotor, such as the pivot zone or point of a rotor, can lead to information uncertainty in a bipolar electrogram from that part. For instance, the changing wave front direction near the pivot zone or point may cause a broader distribution in the bipolar voltage histogram. This may cause a pivot point or zone to have a higher kurtosis value when compared to signals from the periphery of the rotor.

Kurtosis measures the distribution of signal values from electrograms within the histogram. Each electrogram from different spatial location can be binned, such as by using a bin size of 0.001 mV, according to its amplitude into a voltage histogram (as shown in FIGS. 14 and 15). Then, the relative probability density 'p' may be defined, such as according to the number of counts in an amplitude bin divided by the sum of bin counts in all the bins. kurtosis values can be calculated for the intra-atrial electrograms or other types of datasets using the equations described in this section.

The kurtosis values estimated using the equations of this section can then be used to generate a 2D or 3D kurtosis map depending on the implementation, such as shown in FIG. 13. The kurtosis map can then be displayed via a display device at 1008. The kurtosis map can continuously update itself as new time series data is inputted into the system or as the analysis of symbols at 1006 reoccurs. Note that 1006a and 1006b may be sub-operations of 1006. Also, note that 1004a, 1004b, and 1004c may be sub-operations of 1004.

The EMD Approach

Figure 16:
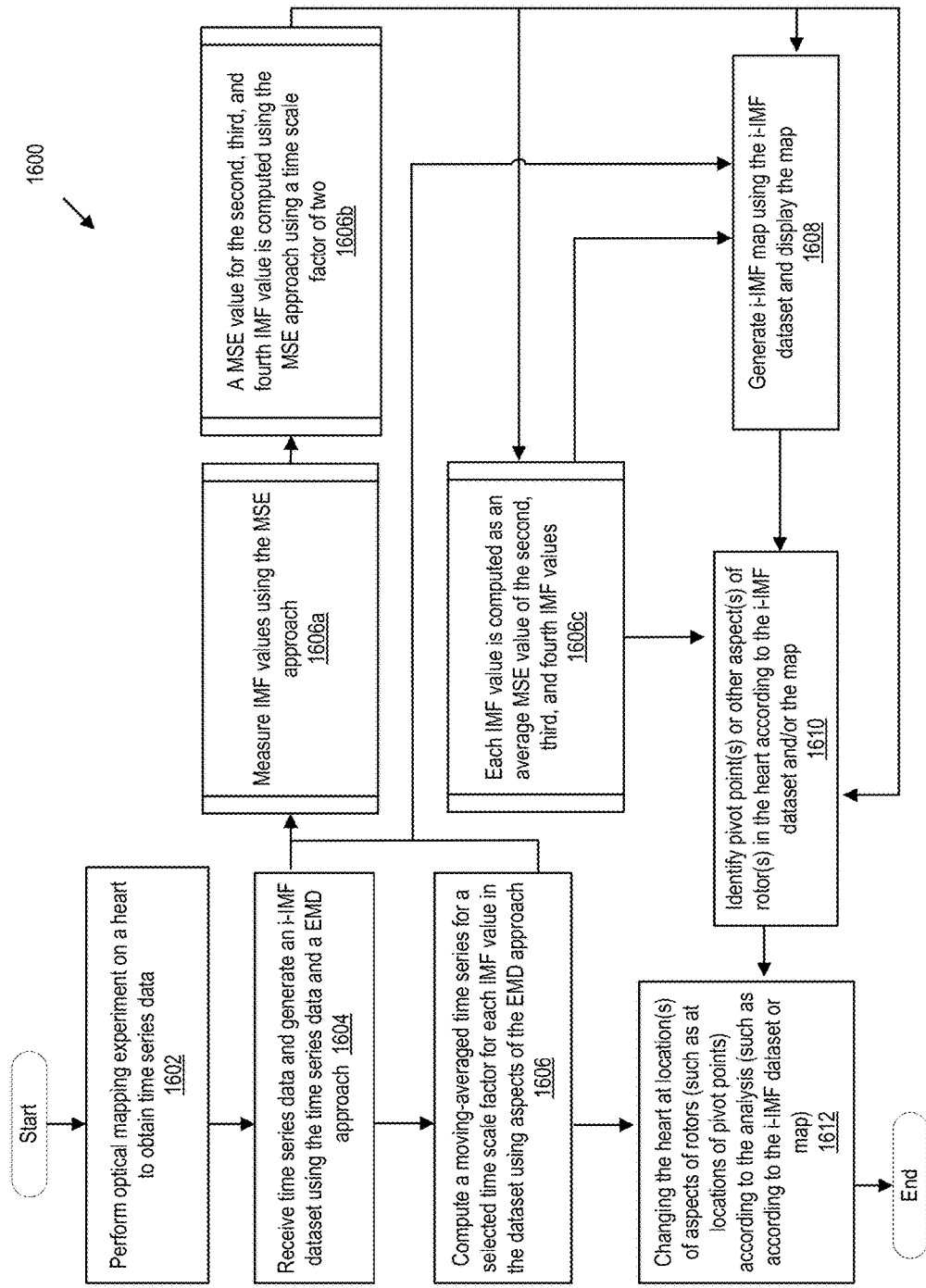
FIG. 16 illustrates exemplary operations performed by a system that can implement rotor identification in a fibrillation, such as an atrial fibrillation, using EMD calculations.

FIG. 16 illustrates exemplary operations 1600 performed by a system that can implement rotor identification in a fibrillation, such as atrial or ventricular fibrillation, and treat the fibrillation accordingly. Operations 1600 form a method for identifying and treating a pivot point or some other aspect of a rotor in a fibrillation (such as an atrial or ventricular fibrillation). The operations 1600 include performing an optical mapping experiment feasible on human or animal hearts, including any in vivo or in vitro experiment to obtain time series data, at 1602. As mentioned, FIG. 3 illustrates an example of a single rotor in an isolated rabbit heart from optical mapping experiments. In FIG. 3, the pivot point of the rotor is indicated by an arrow. FIG. 3 is an exemplary snapshot of a phase movie, where different colors represent different phases of action potential. The convergence of different phases may correspond to a singularity point, e.g., the pivotal point or core of the rotor, which can be identified by the arrow.

The operations 1600 include receiving, by a processor (such as CPU 402 illustrated in FIG. 4), at 1604, the time series data obtained from a plurality of electrograms or electrical potential readings of a heart. As mentioned herein, the electrograms can be derived from electrical potential readings, such as those described herein. In instances using electrograms, each electrogram of the plurality of electrograms corresponds to a different spatial location (such as a different unique spatial location) in the heart and each electrogram of the plurality of electrograms includes a plurality of electrical potential readings over a time series. These readings may be voltage readings (such as shown by chart 502a of FIG. 5). Also, different locations in the heart are represented by respective sets of data.

Additionally, at 1604 (not depicted), the processor may generate histograms using the sets of data and the symbolic dynamics approach disclosed herein. The symbolic dynamics approach may include binning each electrogram of the plurality of electrograms (such as binning each set of electrical potentials) according to amplitude, which results in a plurality of bins per electrogram. Each bin of the plurality of bins represents an amplitude or amplitude range of the electrical potentials and includes a frequency of occurrences of the amplitude or amplitude range. The bins may be displayed as a histogram, such as shown by histogram 502b of FIG. 5. The operation at 1604 may also include determining a probability density of each bin of the plurality of bins, per electrogram (not depicted). The histogram may also be displayed after the determination of the probability densities.

Also, at 1604, a processor of the system determines a i-IMF dataset using the time series data. Further, the i-IMF dataset may be determined using the probability densities from the symbolic dynamics approach. In an example, with the determination of the i-IMF dataset, the processor may generate a two-dimensional (2D) i-IMF map (such as shown in FIG. 20). For example, the processor may use the time series data or the probability densities. Operation 1604 may also include displaying the 2D i-IMF map. In some examples, a three-dimensional (3D) image of the heart may be generated and/or displayed as well.

At 1604, the processor may determine an i-IMF dataset using the EMD approach and the time series data. In an example, with the determination of i-IMF, the processor may generate a 2D i-IMF map (such as shown in FIG. 20) using the EMD approach too. Input for the EMD approach can include 2D DF maps as well. The EMD approach is described in this section in more detail below, with reference to operations 1604, 1606, 1606a-1606c, and 1608.

At 1610, in an example, the processor can identify a pivot point or another indicator part of a rotor in a fibrillation according to the analysis and determinations of operations 1604-1608. For example, where the processor automatically identifies a pivot point or some other indicator part of the rotor, an actual map may not be displayed and identification of the pivot point or the other indicator part may be solely according to the analysis and determinations of operations 1604-1606 and 1606a-1606c. In other words, in automated identification of a rotor part, displaying of the map at 1608 can be excluded. Alternatively, or additionally, at 1610, the processor can identify a pivot point or another type of indicator part according to one or more of the maps describe herein. For example, at 1604 or 1606, the processor can optionally communicate any one of the maps described herein to a display device communicatively coupled to the processor, and the display device can then display one or more of the maps. Then, according to one or more of the maps, the processor automatically (or a user manually) can identify a pivot point or another type of indicator part of a rotor in a fibrillation, such as at 1610.

At 1612, a condition of the heart can then be treated according to at least the identified indicator part of the rotor. In an exemplary embodiment, the treating of the condition of the heart can include ablating the heart according to at least the identified indicator part of the rotor. For example, a catheter-based ablation procedure that is customized for the patient can be designed according to at least the identified indicator part of the rotor.

With EMD approach, at operation 1608, the processor may generate an i-IMF map (such as shown in FIG. 20) according to calculations of EMD approach and the MSE approach, as well as use the i-IMF dataset as input. The MSE approach is described in detail in the next section.

The EMD approach is a method that is specifically designed to handle both nonlinear and non-stationary signals, such as electrograms and the signal energy associated with various intrinsic mode functions (IMFs) on various time scales are directly extracted. The Higher the complexity of the signal, more IMFs are used to describe the signal. Once the non-stationary signal is decomposed using EMD to obtain the IMFs the complexity of the IMFs are quantified such as by using a Lyapunov exponent, entropy, or a correlation dimension. As mentioned, intra-atrial electrograms with rotors are highly chaotic and specifically, the rotor pivot region is highly chaotic compared to the periphery. Therefore, any mapping method that attempts to capture the rotor core area should provide better contrast in the complexity parameter measured between the rotor pivot area and the periphery.

The EMD approach can be applied to the optical data from imaging the electrical activity of an isolated heart, as well as intra-atrial electrograms obtained from patients to measure its complexity to identify rotor core region such as the rotor depicted in FIGS. 3 and 11. FIG. 11, for example, shows an example of a single rotor where pixel '1' represents the rotor pivot point and pixel '2' corresponds to rotor periphery. Chaotic distribution of the optical intensities can be noted at pixel '1' at the rotor pivot point (see FIG. 11 top panel) while a more uniform intensity distribution is seen at pixel '2' (see FIG. 11, bottom panel). Therefore, it can be expected that more IMFs are used to decompose the signal near the rotor core area compared to the periphery. The complexity of the IMFs can be measured using aspects of the MSE approach at 1606a and the complexity index of the IMF (i-IMF) determined at 1604. Higher i-IMF values are expected at the rotor core region and relatively lower i-IMF values in the periphery, which can enable accurate identification of the rotor core region.

Figure 17:
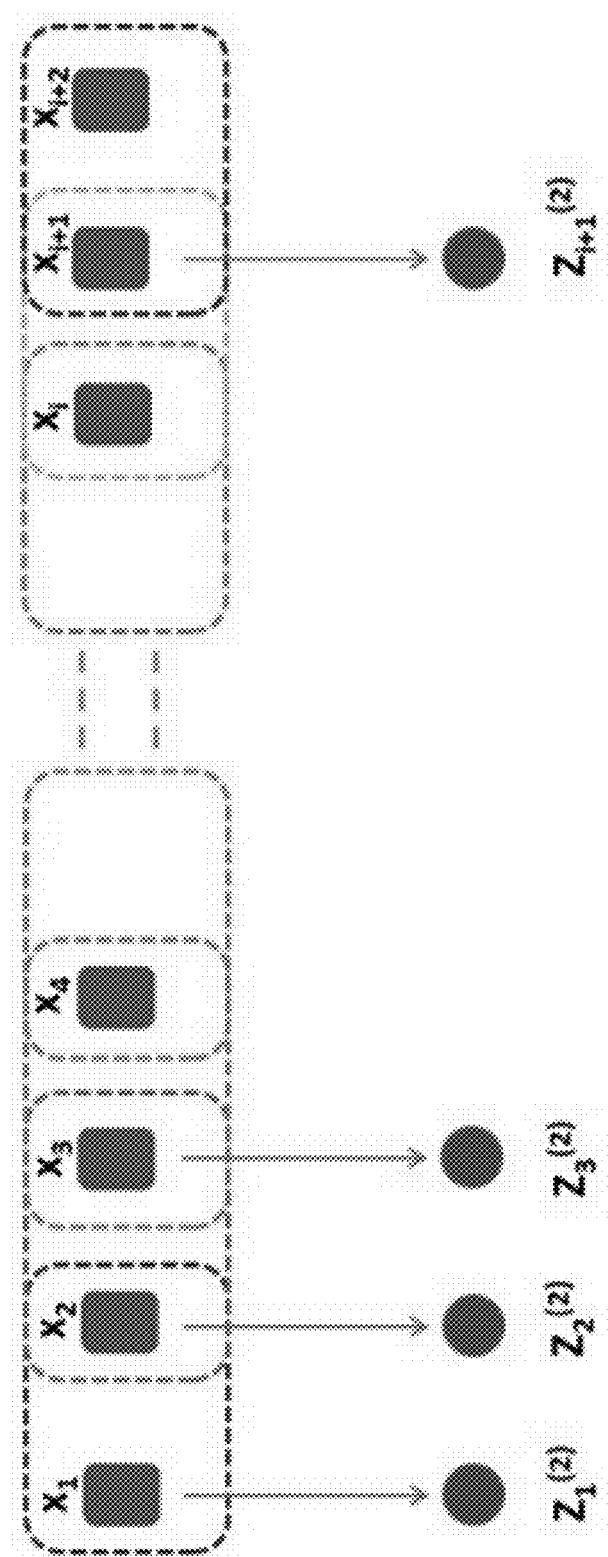
FIG. 17 shows a schematic illustration of an exemplary production of a moving average time series with a scale factor of two, which is used by the EMD and MSE approaches. The filled-in squares with rounded corners represent raw time series data and the filled-in circles represent nearest neighbor moving-averaged time series.

With the EMD approach, let $x=\{x_2, x_3 \ldots x_N\}$ represent the electrogram time series of length N. First, EMD is applied to the time series data and the IMFs are computed, which results in an i-IMF dataset at 1604. Next, for each IMF moving-averaged time series $z^\tau$ is computed for the chosen time scale factor 'τ' as illustrated in FIG. 17 using Equation (1) of this section, which is the following equation:

$$Z_j^\tau = \frac{1}{(\tau)} \sum_{i=j}^{\tau+j-1} X_i \quad (1)$$

where, $1 \le j \le N_{-\tau}$ and $i = 1, 2, 3, \ldots N$

At 1606b, a MSE value for the second, third, and fourth IMF is computed using the MSE approach using a scale factor τ=2. At 1606c, i-IMF, or the IMF value is computed as the average MSE value of the second, third, and fourth IMF values, which can capture the complexity. The procedure can be repeated for the whole set of optical data to produce a 2D i-IMF map (such as the map shown in FIG. 20) to visually locate the rotor core area which is expected to have high i-IMF compared to the periphery. In other words, the EMD approach can include computing a moving-averaged time series for a selected time scale factor for each IMF value in the IMF dataset at 1606, measuring IMF values using the MSE approach at 1606a (which can be a sub-operation of 1604 or 1606), computing a MSE value for the second, third, and fourth IMF value using the MSE approach as well as a time scale factor of two at 1606b (which can be a sub-operation of 1604 or 1606), and computing each IMF value as an average MSE value of the second, third, and fourth IMF values at 1606c (which can be a sub-operation of 1604 or 1606).

Figure 18:
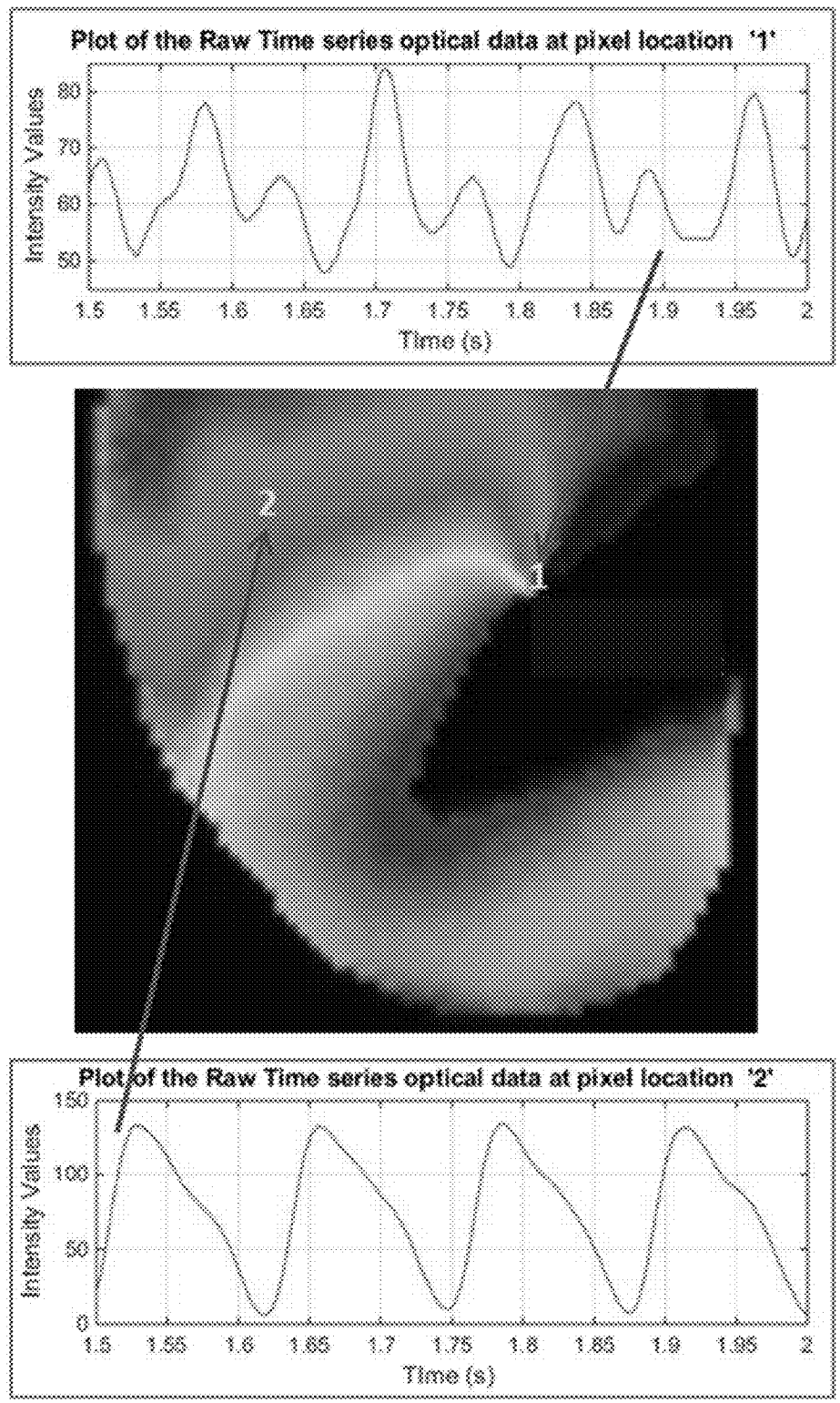
FIGS. 18-20 are depicted to show graphical differences between a snapshot of a phase movie from an optical mapping animal experiment (shown in FIG. 18) and a DF map (shown in FIG. 19) and an i-IMF map (shown in FIG. 20). These figures illustrate exemplary graphics identifying the rotor and its pivot point using a DF map and a i-IMF map respectively, wherein each of these maps is derived from optical mapping data corresponding to the rotor depicted in FIG. 18.
Figure 19:
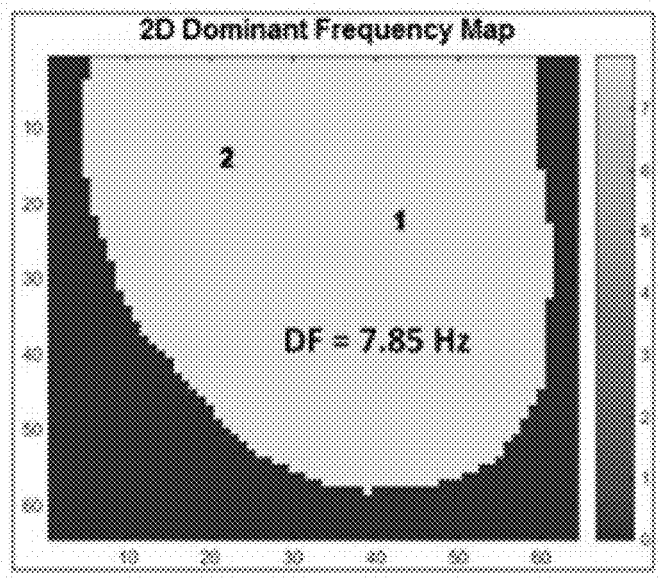

In comparison to the snapshot shown in FIG. 18, FIG. 19 shows the 2D DF map with uniform DF=7.85 Hz thereby unable to identify rotor core region, and FIG. 20 shows the 2D i-IMF map where the pivot point of the rotor has higher values compared to periphery with relatively higher so that the pivot point is more identifiable.

Figure 21:
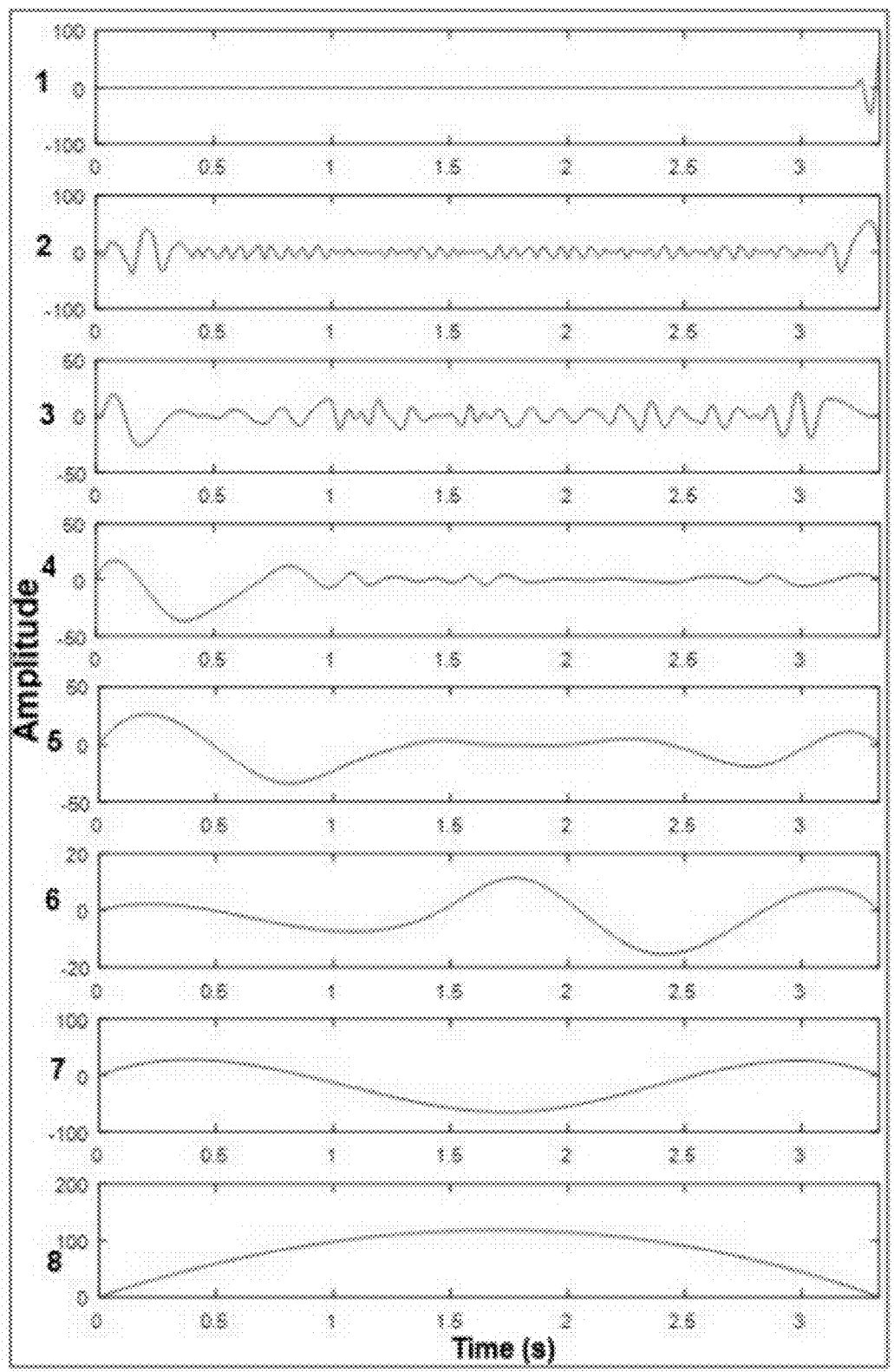
FIG. 21 illustrates eight exemplary intrinsic mode functions (8 IMFs) for the optical electrogram at a rotor pivot point, such as at pixel location labeled "1" in FIG. 11.
Figure 22:
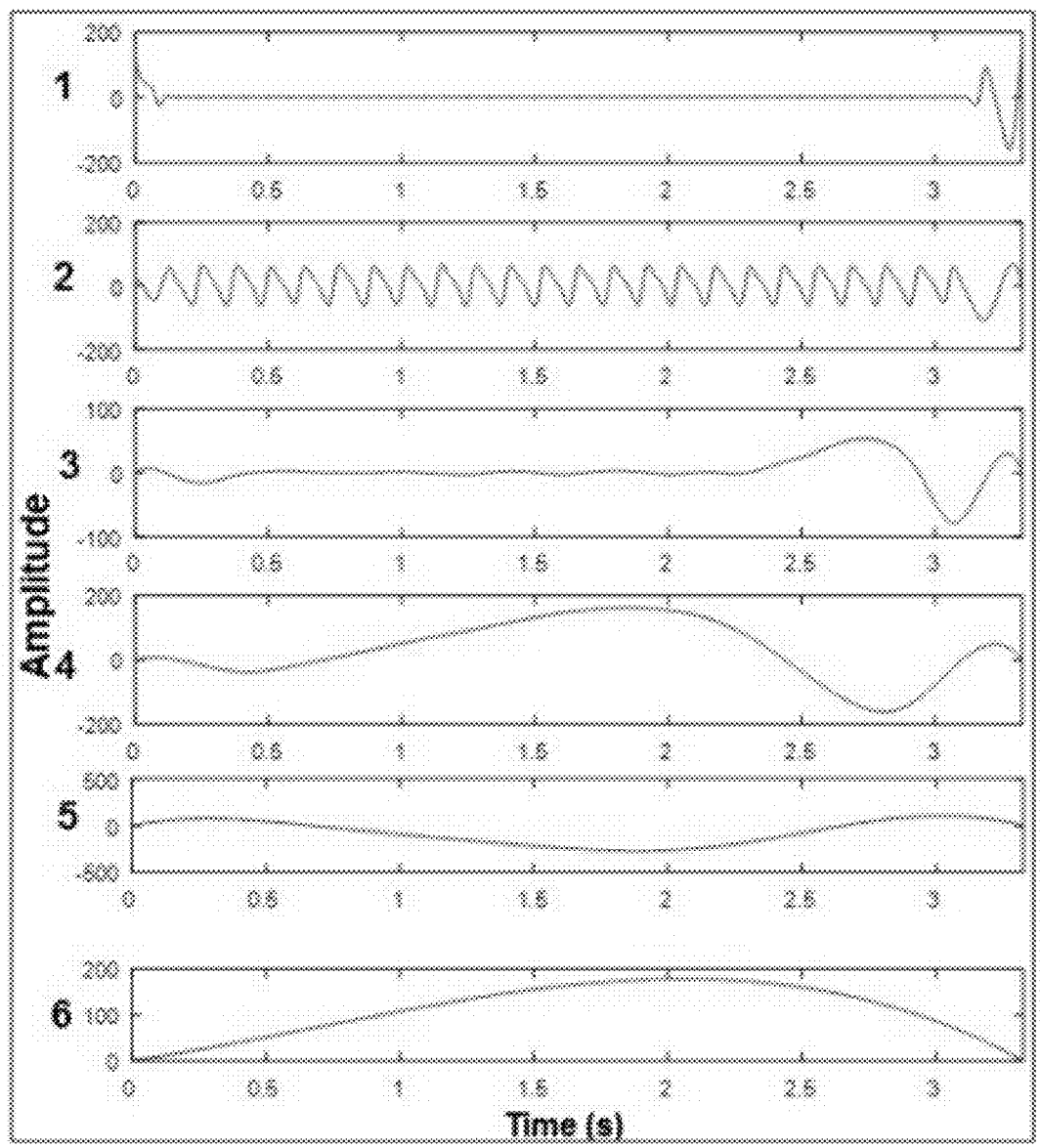
FIG. 22 illustrates six exemplary intrinsic mode functions (6 IMFs) for the optical electrogram at an out region point of the rotor, such as at pixel location labeled "2" in FIG. 11.

FIGS. 21 and 22 show the IMFs generated from EMD approach, with eight and six IMFs at pixel location '1' and '2', respectively. IMFs 2, 3 and 4 at both pixel locations represent the complexity of the optical data which was quantified as i-IMF values using the MSE approach. As mentioned, FIG. 20 shows a normalized 2D i-IMF map showing location of the pivot point indicated by the arrow.

The MSE Approach

Figure 23:
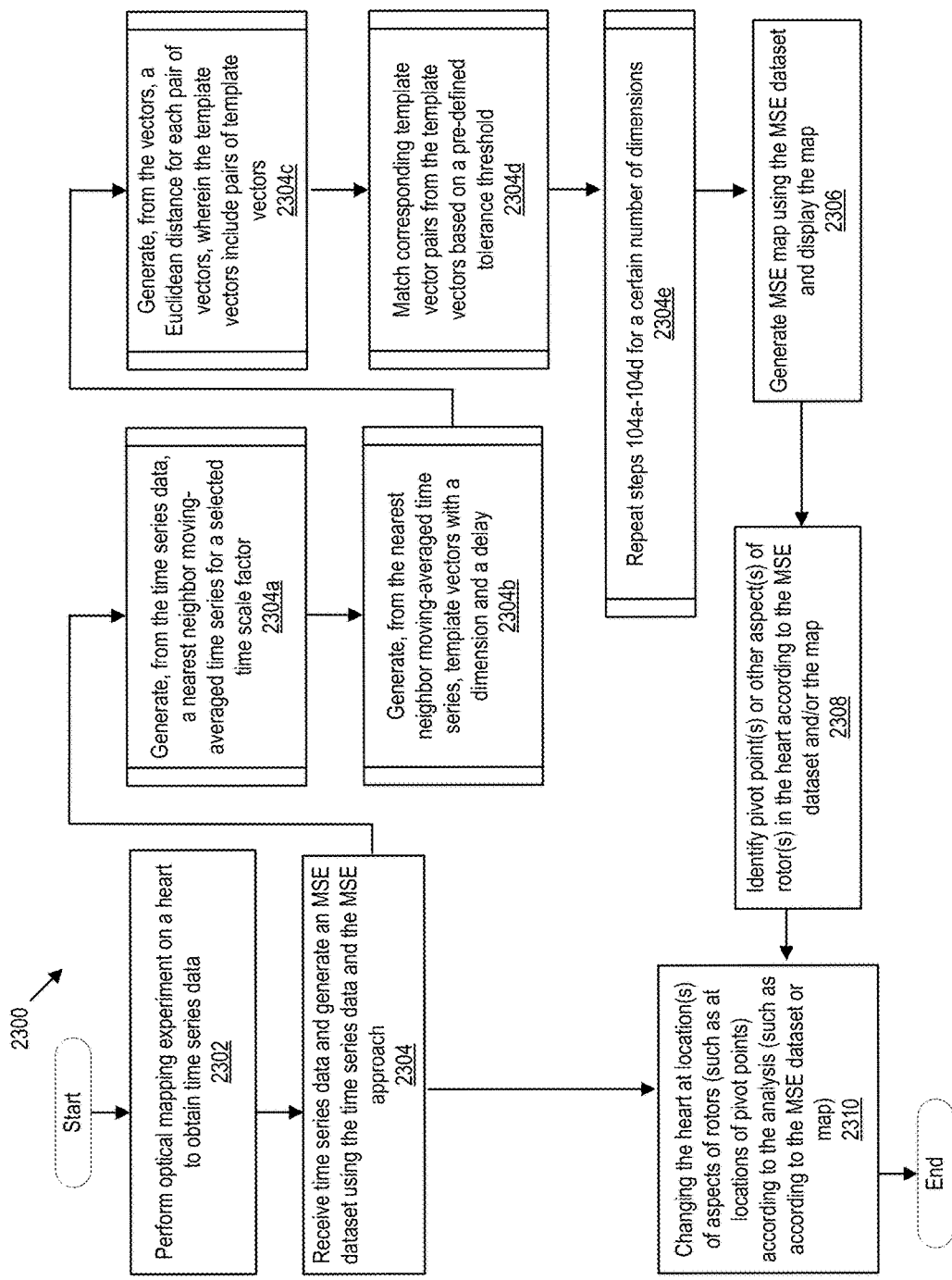
FIG. 23 illustrates exemplary operations performed by a system that can implement rotor identification in a fibrillation, such as an atrial fibrillation, using MSE calculations.

FIG. 23 illustrates exemplary operations 2300 performed by a system that can implement rotor identification in a fibrillation, such as atrial or ventricular fibrillation, and treat the fibrillation accordingly. Operations 2300 form a method for identifying and treating a pivot point or some other aspect of a rotor in a fibrillation (such as an atrial or ventricular fibrillation). The operations 2300 include performing an optical mapping experiment feasible on human or animal hearts, including any in vivo or in vitro experiment to obtain time series data, at 2302. As mentioned, FIG. 3 illustrates an example of a single rotor in an isolated rabbit heart from optical mapping experiments. In FIG. 3, the pivot point of the rotor is indicated by an arrow. FIG. 3 is an exemplary snapshot of a phase movie, where different colors represent different phases of action potential. The convergence of different phases may correspond to a singularity point, e.g., the pivotal point or core of the rotor, which can be identified by the arrow.

The operations 2300 include receiving, by a processor (such as CPU 402 illustrated in FIG. 4), at 2304, the time series data obtained from a plurality of electrograms or electrical potential readings of a heart. As mentioned herein, the electrograms can be derived from electrical potential readings, such as those described herein. In instances using electrograms, each electrogram of the plurality of electrograms corresponds to a different spatial location (such as a different unique spatial location) in the heart and each electrogram of the plurality of electrograms includes a plurality of electrical potential readings over a time series. These readings may be voltage readings (such as shown by chart 502a of FIG. 5). Also, different locations in the heart are represented by respective sets of data.

Additionally, at 2304 (not depicted), the processor may generate histograms using the sets of data and the symbolic dynamics approach disclosed herein. The symbolic dynamics approach may include binning each electrogram of the plurality of electrograms (such as binning each set of electrical potentials) according to amplitude, which results in a plurality of bins per electrogram. Each bin of the plurality of bins represents an amplitude or amplitude range of the electrical potentials and includes a frequency of occurrences of the amplitude or amplitude range. The bins may be displayed as a histogram, such as shown by histogram 502b of FIG. 5. The operation at 2304 may also include determining a probability density of each bin of the plurality of bins, per electrogram (not depicted). The histogram may also be displayed after the determination of the probability densities.

Also, at 2304, a processor of the system generates an MSE dataset using the time series data and the MSE approach. In addition, the MSE dataset may be determined using the probability densities from the symbolic dynamics approach. In an example, with the determination of the MSE dataset, the processor may generate a two-dimensional (2D) MSE map (such as shown in FIGS. 25-27). For example, the processor may use the time series data or the probability densities to generate such maps. Operation 2304 may also include displaying one or more MSE maps. In some examples, a three-dimensional (3D) image of the heart may be generated and/or displayed as well. Furthermore, input for the MSE approach can include 2D DF maps. The MSE approach is described in this section in more detail below, with reference to operations 2304, 2304a-2304e, and 2306.

At 2308, in an example, the processor can identify a pivot point or another indicator part of a rotor in a fibrillation according to the analysis and determinations of operations 2304, 2304a-2304e, and 2306. For example, where the processor automatically identifies a pivot point or some other indicator part of the rotor, an actual map may not be displayed and identification of the pivot point or the other indicator part may be solely according to the analysis and determinations of operations 2304 and 2304a-2304e. In other words, in automated identification of a rotor part, displaying of the map at 2306 can be excluded. Alternatively, or additionally, at 2308, the processor can identify a pivot point or another type of indicator part according to one or more of the maps describe herein. For example, the processor can optionally communicate any one of the maps described herein to a display device communicatively coupled to the processor, and the display device can then display one or more of the maps. Then, according to one or more of the maps, the processor automatically (or a user manually) can identify a pivot point or another type of indicator part of a rotor in a fibrillation, such as at 2308.

At 2310, a condition of the heart can then be treated according to at least the identified indicator part of the rotor. In an exemplary embodiment, the treating of the condition of the heart can include ablating the heart according to at least the identified indicator part of the rotor. For example, a catheter-based ablation procedure that is customized for the patient can be designed according to at least the identified indicator part of the rotor.

With MSE approach, at operation 2306, the processor may generate one or more MSE maps (such as shown in FIGS. 25-27) according to calculations of MSE approach, as well as use the MSE dataset as input for the maps.

The MSE approach can be an enhancement to a Shannon Entropy (SE) approach (such as the SE approach described in U.S. non-provisional patent application Ser. No. 15/373,193, filed Dec. 8, 2016). A possible limitation of the SE approach is related to the specific characteristics of the cardiac electrograms. With the symbolic dynamics approach various entropy based measures (such as SE, Kolmogorov entropy, spectral entropy, wavelet entropy, permutation entropy, approximate entropy, and sample entropy) can provide capturing intrinsic dynamics of non-stationary time series data to quantify complexity of such data. However, it has been shown that these different entropy estimates may be effective for long time series, and may not efficiently capture the complexities for shorter nonstationary time series data in some scenarios. For example, AF electrograms can often be captured for three to eight second, which may be considered relatively short non-stationary time series data. Thus, in some situations the SE approach and other entropy-based approaches may be less effective at identifying a rotor pivot point with the relatively short non-stationary time series data.

On the other hand, the MSE approach with a modification that includes estimating new time series with a nearest neighbor moving average kernel that uses information from the 'past' and 'future' value, may more effectively capture the intrinsic dynamics of the relatively short non-stationary time series. The modification can include a time scale factor that extends to both sides of a time series point in reference.

The MSE approach can use a sample entropy algorithm (such as an SE algorithm) over multiple time scales to fully capture the intrinsic complexity of non-stationary time series data. The MSE approach can also use a nearest neighbor moving average kernel to capture the complexity of a non-stationary time series data. State or "memory" of the time series data is accounted for by taking into account the past and future time series values while computing the nearest neighbor average. The MSE approach, thus, can include a time scale factor that represents time scaling in both forward and reverse directions with reference to a particular point in time. An exemplary embodiment of the MSE approach is provided in this section below.

Figure 24:
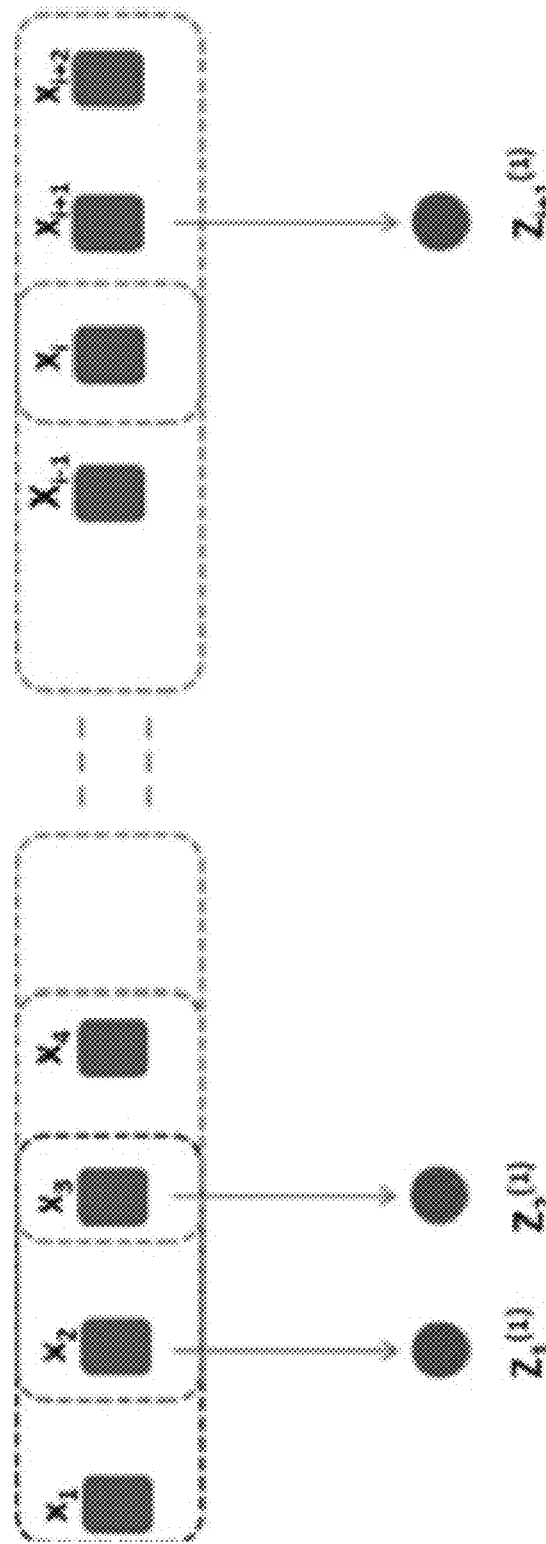
FIG. 24 shows a schematic illustration of an exemplary production of a moving average time series with a scale factor of one, which is used by at least an exemplary embodiment of the MSE approach. The filled-in squares with rounded corners represent raw time series data and the filled-in circles represent nearest neighbor moving-averaged time series.

With the MSE approach, let $x=\{x_1, x_2, x_3 \ldots x_N\}$ represent the electrogram time series of length N, and first a nearest neighbor moving-averaged time series $z^\tau$ is computed for the chosen time scale factor '$\tau$' as illustrated in FIG. 24 using the following Equation (1) of this section.

$$Z_j^\tau = \frac{1}{(\tau)} \sum_{i=j}^{\tau+j-1} X_i \qquad (1)$$

where, $1 \le j \le N_{-\tau}$ and $i = 1, 2, 3, \ldots N$

Second, template vectors $y^m_k(\delta)$ with dimension m and delay $\delta$ are constructed from $z^\tau$ using Equation (1) of this section at each specific $\tau$ as provide in the following Equation (2) of this section.

$$y_k^m(\delta) = \{Z_k Z_{k-\delta} \ldots Z_{k+(m-1)\delta}\}, \qquad (2)$$

where $1 \le k \le N_{-m\delta}$

Then, the Euclidean distance $d_{ij}^m$ for each pair of template vectors $\{y_i^m, y_j^m\}$ is calculated using the infinity norm as show below in Equation (3) of this section.

$$d_{ij}^m(\delta) = \|y_i^m(\delta) - y_j^m(\delta)\|_\infty, \quad (3)$$

where $1 \leq i, j \leq N_{-m\delta}$, and $j > i+\delta$

Next, matched template vector pairs $\{y_i^m, y_j^m\}$ are computed based on a pre-defined tolerance threshold r as show below in Equation (4) of this section.

$$d_{ij}^m(\delta) \leq r \quad (4)$$

The value for r is selected, such as selected as 0.2 times the standard deviation of the raw time series x. The delay factor $\delta$ can be selected as well, such as selected as 1. The total number of matched template vectors can be computed and denoted by n (m, $\delta$, r). The Equations (2)-(4) can be repeated for m+1 dimensions, and the total number of matched template vectors can be computed. The total number of matched template vectors can be denoted by n (m+1, $\delta$, r) with the repeat for m+1 dimensions.

Finally, MSE values can be calculated with the following Equation (5) of this section, shown below.

$$MSE(x, m, \delta, r) = -\ln \frac{n(m+1, \delta, r)}{n(m, \delta, r)} \quad (5)$$

wherein n(m+1, $\delta$, r) is the total number of matched template vectors.

The MSE approach can be applied various nonstationary time series data. The MSE approach can be applied to the optical fluorescence recordings obtained during imaging of an electrical activity of an isolated heart as well as be applied to intra-atrial electrograms obtained from patients. For instance, time series data across all the frames for each pixel point can be obtained and processed using a notch filter, such as a 60 Hz notch filter, to remove noise, such as noise at the 60 Hz. Such time series data can be inputted with the MSE approach and a 2D MSE map can be generated using the MSE value at each pixel location across all the frames. FIGS. 25, 26, and 27 show 2D MSE maps that were generated for scale factors T=1, 2 and 3, respectively.

Noted Successes

Experiments in accordance with embodiments of the method have been performed, such as those discussed in: (1) "Kurtosis as a statistical approach to identify the pivot point of the rotor", 2016 38th Annual International Conference of the IEEE Engineering in Medicine and Biology Society (EMBC), August 2016, dio: 10.1109/EMBC.2016.7590748 (2) "Novel Multiscale Frequency Approach to Identify the Pivot Point of the Rotor", Journal of Medical Devices 10(2):020948, May 2016, doi: 10.1115/1.4033148; and (3) "Rotor Pivot Point Identification with Intrinsic Mode Function Complexity Index using Empirical Mode Decomposition", Student Conference (ISC), 2016 IEEE EMBS International, May 2016, doi: 10.1109/EMBSISC.2016.7508597. Such experiments have shown evidence of the successes using some of the disclosed techniques. Techniques based on entropy, kurtosis, and the other approaches mentioned herein can correctly identify self-sustaining regions of chaotic rhythms in at least animal models of arrhythmia. Also, experimental verification of the feasibility of using a such mapping techniques to identify self-sustaining points of rotors in isolated animal hearts has been successful. Further, the approaches disclosed herein that have been applied to clinical intracardiac electrograms from a patient with persistent AF to construct maps have been successful.

What is claimed is:

1. A method, comprising:
   receiving, using a processor, an electrogram for each of a plurality of spatial locations in a heart, each electrogram comprising time series data including a plurality of electrical potential readings over time;
   generating, from the time series data, a dataset, the dataset including a plurality of values using a mathematical approach, wherein the mathematical approach is either a multi-scale frequency (MSF) approach, a kurtosis approach, an empirical mode decomposition (EMD) approach, or a multi-scale entropy (MSE) approach; and
   graphically indicating pivot points of rotors associated with atrial or ventricular fibrillation according to the dataset;
   wherein the dataset is a first dataset, the plurality of values is a first plurality of values, and the mathematical approach is a first mathematical approach, and wherein the method further comprises:
   generating, from the time series data, a second dataset, the second dataset including a second plurality of values using a second mathematical approach that is different from the first mathematical approach, wherein the second mathematical approach is either a multi-scale frequency (MSF) approach, a kurtosis approach, an empirical mode decomposition (EMD) approach, or a multi-scale entropy (MSE) approach depending on the first mathematical approach used; and
   graphically indicating pivot points of rotors associated with atrial or ventricular fibrillation according to the second dataset.

2. The method of claim 1, wherein the graphically indicating pivot points of rotors comprises generating, from the generated dataset, a map including a plurality of graphical indicators of the plurality of generated values at the plurality of spatial locations in the heart,
   wherein the map includes an image of the heart and a graphical indication of a location of a pivot point of a rotor in the heart, and
   wherein the plurality of graphical indicators of the plurality of values include a range of different colors, shades of a gray or another color, different symbols, or indexed values each of the range corresponding to a value such that the displaying of the plurality of graphical indicators shows MSF levels, kurtosis levels, EMD levels, or MSE levels at different locations in the heart depending on the mathematical approach used.

3. The method of claim 2, further comprising displaying the plurality of graphical indicators using a display device.

4. The method of claim 1, further comprising physically changing the heart at one or more of the plurality of spatial locations in the heart according to the generated dataset.

5. The method of claim 4, wherein the changing of the heart includes catheter ablations at the one or more of the plurality of spatial locations in the heart.

6. The method of claim 1, further comprising performing the plurality of electrograms at the plurality of spatial locations in the heart to obtain the time series data.

7. The method of claim 1, wherein the plurality of electrograms is derived from an optical mapping experiment on the heart.

8. A method, comprising:
  receiving, using a processor, an electrogram for each of a plurality of spatial locations in a heart, each electrogram comprising time series data including a plurality of electrical potential readings over time;
  generating, from the time series data, a dataset including a plurality of values using a multi-scale frequency (MSF) approach comprising:
    generating, from the time series data, a dominant frequency (DF) dataset including a plurality of DF values corresponding to the plurality of spatial locations in the heart;
    generating a multi-scale frequency index (i-MSF) using the DF dataset; and
    generating an i-MSF dataset according to the DF dataset, wherein the i-MSF dataset includes a plurality of i-MSF values; and
  graphically indicating pivot points of rotors associated with atrial or ventricular fibrillation according to the dataset;
  wherein the MSF approach includes use of band-pass quadrature filters, and use of a Hilbert transform operation to generate the i-MSF dataset by weighting various frequency components from the filters.

9. The method of claim 8, further comprising physically changing the heart at one or more of the plurality of spatial locations in the heart according to the generated dataset.

10. A method comprising:
  receiving, using a processor, an electrogram for each of a plurality of spatial locations in a heart, each electrogram comprising time series data including a plurality of electrical potential readings over time;
  generating, from the time series data, a dataset including a plurality of values using a multi-scale frequency (MSF) approach comprising:
    generating, from the time series data, a dominant frequency (DF) dataset including a plurality of DF values corresponding to the plurality of spatial locations in the heart;
    generating a multi-scale frequency index (i-MSF) using the DF dataset; and
    generating an i-MSF dataset according to the DF dataset, wherein the i-MSF dataset includes a plurality of i-MSF values; and
  graphically indicating pivot points of rotors associated with atrial or ventricular fibrillation according to the dataset;
  wherein the MSF approach includes use of band-pass quadrature filters and
  use of a Hilbert transform operation to generate the i-MSF dataset by weighting various frequency components resulting from the filters.

11. A method comprising:
  receiving, using a processor, an electrogram for each of a plurality of spatial location in a heart, each electrogram comprising time series data including a plurality of electrical potential readings over time;
  generating, from the time series data, a dataset including a plurality of values using a multi-scale frequency (MSF) approach comprising:
    generating, from the time series data, a dominant frequency (DF) dataset including a plurality of DF values corresponding to the plurality of spatial locations in the heart;
    generating a multi-scale frequency index (i-MSF) using the DF dataset; and
    generating an i-MSF dataset according to the DF dataset, wherein the i-MSF dataset includes a plurality of i-MSF values; and
  graphically indicating pivot points of rotors associated with atrial or ventricular fibrillation according to the dataset;
  wherein the MSF approach includes using Log-Gabor filters and the following equation:

$$i\text{-}MSF = \rho_o \left[ \sum_{i=1}^{N-1} q_i \right]^{-1} \sum_{i=1}^{N-1} 2^{i+0.5} q_{i+1}$$

wherein $q_i$ is an output of an ith Log-Gabor filter and $\rho_o$ is the center frequency of the first Log-Gabor filter, and wherein:
    (i) the Log-Gabor filters include a one-dimensional Log-Gabor function with a frequency response provided by the following equation:

$$G(f) = \exp\left( \frac{-(\log(f/f_0))^2}{2(\log(\sigma/f_0))^2} \right)$$

wherein $f_0$ is the center frequency and $\sigma$ is related to bandwidth (B), and wherein when it is determined to maintain a same shape while the frequency parameter is varied, the ratio $\sigma/f_0$ is configured to remain constant;
    (ii) the Log-Gabor filters include a one-dimensional Log-Gabor function with a frequency response provided by the following equation:

$$G(f) = \frac{f_0}{f} \exp\left( \frac{-(\log(f/f_0))^2}{2(\log(\sigma/f_0))^2} \right)$$

wherein $f_0$ is the center frequency and $\sigma$ a is related to bandwidth (B), wherein, $B = 2\sqrt{2/\log(2)}(\|\log(\sigma_f/f_0)\|)$, and wherein
      when it is determined to maintain a same shape while the frequency parameter is varied, the ratio $\sigma/f_0$ is configured to remain constant; or
    (iii) the Log-Gabor filters include a two-dimensional Log-Gabor function with a frequency response provided by the following equation:

$$G(f, \theta) = \exp\left( \frac{-(\log(f/f_0))^2}{2(\log(\sigma_f/f_0))^2} \right) \exp\left( \frac{-(\theta - \theta_0)^2}{2\sigma_\theta^2} \right)$$

wherein $f_0$ is the center frequency, $\sigma$ is the width parameter related to bandwidth (B) for the frequency, $\theta_0$ is the center orientation, and $\sigma_\theta$ is the width parameter related to bandwidth (B) of the orientation, and wherein $B = 2\sqrt{2/\log(2)}(\|\log(\sigma_f/f_0)\|)$, and wherein $B_\theta = 2\sigma_\theta \sqrt{2\log 2}$.

12. A method, comprising:
  receiving, using a processor, an electrogram for each of a plurality of spatial locations in a heart, each electrogram comprising time series data including a plurality of electrical potential readings over time;

generating, from the time series data, a dataset including a plurality of values using a kurtosis approach comprising:

generating, from the time series data, a probability density function (PDF);

generating, from the PDF, a kurtosis dataset; and generating a kurtosis value or a value related to the fourth central moment of the PDF according to the following equation:

$$Kurt(X) = E\left\{\left[\frac{X - E\{X\}}{\sigma}\right]^4\right\} = \frac{\mu_X^4}{\sigma_X^4}$$

wherein x represents the time series data, wherein μ is the central moment and $\mu^4$ is the fourth central moment, σ is the standard deviation, E is the expectation value or mean of a stochastic variable X, as determined by using the following equation:

$$E\{X\} = \int_{-\infty}^{\infty} x \cdot f(x)dx = \mu_X$$

and wherein f is the PDF; and graphically indicating pivot points of rotors associated with atrial or ventricular fibrillation according to the dataset.

13. The method of claim 12, further comprising physically changing the heart at one or more of the plurality of spatial locations in the heart according to the generated dataset.

14. A method comprising:

receiving, using a processor, an electrogram for each of a plurality of spatial locations in a heart, each electrogram comprising time series data including a plurality of electrical potential readings over time;

generating, from the time series data, a dataset including a plurality of values using an empirical mode decomposition (EMD) approach comprising:

generating, from the time series data, an intrinsic mode functions index (i-IMF) dataset, the i-IMF dataset including a plurality of intrinsic mode function (IMF) values; and for each IMF value, computing a moving-averaged time series for a selected time scale factor; and graphically indicating pivot points of rotors associated with atrial or ventricular fibrillation according to the dataset.

15. The method of claim 14, wherein the computing the moving-averaged time series for a selected time scale factor uses the following equation:

$$Z_j^\tau = \frac{1}{(\tau)} \sum_{i=j}^{\tau+j-1} x_i$$

where $1 \leq j \leq N_{-\tau}$, and i=1,2,3, . . . N, and wherein $Z_j^\tau$ is the moving-averaged time series, τ is the selected time scale factor, and x={x1, x2, x3 . . . xN} represents the time series data of length N, wherein the IMF values are measured using a multi-scale entropy (MSE) approach, wherein a MSE value for the second, third, and fourth IMF value is computed using the MSE approach using a time scale factor of two, and wherein each IMF value is computed as an average MSE value of the second, third, and fourth IMF values.

16. The method of claim 14, further comprising physically changing the heart at one or more of the plurality of spatial locations in the heart according to the generated dataset.

17. A method comprising:

receiving, using a processor, an electrogram for each of a plurality of spatial locations in a heart, each electrogram comprising time series data including a plurality of electrical potential readings over time;

generating, from the time series data, a dataset including a plurality of values using a multi-scale entropy (MSE) approach comprising:

generating, from the time series data, a MSE dataset that includes a plurality of MSE values, and wherein generating the MSE dataset includes:

(i) generating, from the time series data, a nearest neighbor moving-averaged time series for a selected time scale factor that accounts for past and future time series values while computing a nearest neighbor average;

(ii) generating, from the nearest neighbor moving-averaged time series, template vectors with a dimension and a delay;

(iii) generating, from the template vectors, a Euclidean distance for each pair of template vectors, wherein the template vectors include pairs of template vectors;

(iv) matching corresponding template vector pairs from the template vectors based on a pre-defined tolerance threshold; and (v) repeating processes (i)-(iv) for a certain number of dimensions; and graphically indicating pivot points of rotors associated with atrial or ventricular fibrillation according to the dataset.

18. The method of claim 17, wherein the generating a nearest neighbor moving-averaged time series uses the following equation:

$$Z_j^\tau = \frac{1}{(2\tau+1)} \sum_{i=j}^{2\tau+1} x_i$$

where $1 \leq j \leq N_{-\tau}$ and i=1, 2, 3, . . . N, and wherein $Z_j^\tau$ is the nearest neighbor moving-averaged time series, τ is the selected time scale factor, and x={$x_1, x_2, x_3 \ldots x_N$} represents the time series data of length N, wherein the generating template vectors uses the following equation:

$$y_k^m(\delta) = \{Z_k Z_{k+\delta} \ldots Z_{k+(m-1)\delta}\}$$

where $1 \leq k \leq N_{-m\delta}$, and wherein ykm(δ) is the template vectors with dimension m and delay δ, wherein the generating a Euclidean distance includes using an infinity norm operation, and uses the following equation:

$$d_{ij}^m(\delta) = \|y_i^m(\delta) - y_j^m(\delta)\|_\infty$$

where $1 \leq i$, $j \leq N_{-m\delta}$, and $j > i + \delta$, wherein the Euclidean distance is dijm, and each pair of template vectors is {yim, yjm}, wherein the matching corresponding template vector pairs uses the following equation: $d_{ij}^m(\delta) \leq r$, wherein r is the pre-defined tolerance threshold, wherein the certain number of dimensions is m+1 dimensions, wherein the MSE approach further comprises determining a total number of matched template vectors, wherein generating the MSE value of the MSE dataset uses the following equation:

$$MSE(x, m, \delta, r) = -\ln \frac{n(m+1, \delta, r)}{n(m, \delta, r)}$$

and wherein n(m+1, δ, r) is a total number of matched template vectors.

19. The method of claim 17, further comprising physically changing the heart at one or more of the plurality of spatial locations in the heart according to the generated dataset.

* * * * *

UNITED STATES PATENT AND TRADEMARK OFFICE
CERTIFICATE OF CORRECTION

PATENT NO. : 10,362,955 B2
APPLICATION NO. : 15/427349
DATED : July 30, 2019
INVENTOR(S) : Shivaram Poigai Arunchalam and Alena Talkachova It is certified that error appears in the above-identified patent and that said Letters Patent is hereby corrected as shown below:

On the Title Page

Item (56) References Cited
Page 2, Column 2, delete "Habel et al., "The temporal variability of dominant frequency and complex fractionated atrial electrograms constrains be validity of sequential mapping in human atrial fibrillation", Heart Rhythm, vol. 7, No. 5, pp. 586-593, 2010." insert --Habel et al., "The temporal variability of dominant frequency and complex fractionated atrial electrograms constrains the validity of sequential mapping in human atrial fibrillation", Heart Rhythm, vol. 7, No. 5, pp. 586-593, 2010."--.

In the Specification

Column 32, Line 55, delete "$Z_j^\tau = \frac{1}{(\tau)} \sum_{i=j}^{\tau+j-1} X_i$" and insert --$Z_j^\tau = \frac{1}{(2\tau+1)} \sum_{i=j}^{2\tau+1} X_i$,--.

In the Claims

Claim 11
Column 36, Line 40, delete "wherein $f_0$ is the center frequency and σ a is related to bandwith (B), wherein," insert --wherein $f_0$ is the center frequency and σ is related to bandwith (B), wherein,--.

Claim 18
Column 38, Line 41, after "wherein", delete "the".
Column 38, Line 41, after "generating", insert --the--, delete "a".
Column 38, Line 55, after "wherein", delete "the".
Column 38, Line 55, after "generating", delete "a", insert --the--.
Column 38, Line 63, after "wherein", delete "the".
Column 38, Line 63, delete "a", insert --the--.

Signed and Sealed this
Third Day of March, 2020

Andrei Iancu
*Director of the United States Patent and Trademark Office*